US012110509B2

(12) United States Patent
Lee et al.

(10) Patent No.: US 12,110,509 B2
(45) Date of Patent: Oct. 8, 2024

(54) STEM CELL-DERIVED SERTOLI-LIKE CELL, PREPARATION METHOD THEREFOR, AND USE THEREOF

(71) Applicant: CHA UNIVERSITY INDUSTRY-ACADEMIC COOPERATION FOUNDATION, Pocheon-si (KR)

(72) Inventors: Dong Ryul Lee, Seoul (KR); Dong Won Seol, Yongin-si (KR)

(73) Assignee: CHA UNIVERSITY INDUSTRY-ACADEMIC COOPERATION FOUNDATION, Pocheon-si (KR)

( * ) Notice: Subject to any disclaimer, the term of this patent is extended or adjusted under 35 U.S.C. 154(b) by 781 days.

(21) Appl. No.: 16/811,086

(22) Filed: Mar. 6, 2020

(65) Prior Publication Data

US 2020/0239853 A1 Jul. 30, 2020

Related U.S. Application Data

(63) Continuation-in-part of application No. PCT/KR2018/010525, filed on Sep. 7, 2018.

(30) Foreign Application Priority Data

Sep. 7, 2017 (KR) .......................... 10-2017-0114680

(51) Int. Cl.
*C12N 5/071* (2010.01)
*C12N 5/074* (2010.01)

(52) U.S. Cl.
CPC ......... *C12N 5/0683* (2013.01); *C12N 5/0696* (2013.01); *C12N 2501/115* (2013.01); *C12N 2501/84* (2013.01); *C12N 2506/1346* (2013.01)

(58) Field of Classification Search
None
See application file for complete search history.

(56) References Cited

U.S. PATENT DOCUMENTS

| 2002/0065212 | A1 | 5/2002 | Selawry et al. | |
| 2003/0113910 | A1* | 6/2003 | Levanduski | C12N 5/0696 435/325 |
| 2005/0118145 | A1 | 6/2005 | Dufour et al. | |
| 2009/0028833 | A1 | 1/2009 | John et al. | |
| 2009/0162331 | A1 | 6/2009 | Dufour et al. | |
| 2014/0315305 | A1 | 10/2014 | Shimmura et al. | |
| 2017/0114327 | A1 | 4/2017 | John et al. | |
| 2021/0207099 | A1* | 7/2021 | Millman | C12N 5/0676 |

FOREIGN PATENT DOCUMENTS

| CN | 105087467 | 11/2015 |
| EP | 2496940 | 9/2012 |
| JP | 2007-124923 | 5/2007 |
| WO | WO 97/33470 | 9/1997 |
| WO | WO 2007/089572 A2 | 8/2007 |
| WO | WO 2011/057123 | 5/2011 |
| WO | WO 2011/057128 | 5/2011 |
| WO | WO 2015/155738 | 10/2015 |
| WO | WO 2016/093359 | 6/2016 |
| WO | WO 2005/018540 A2 | 3/2021 |

OTHER PUBLICATIONS

Bucay et al. Stem Cells 27:68-77, 2009 (Year: 2009).*
Printout from https://discovery.lifemapsc.com/library/images/germ-layer-early-derivatives. Printed Nov. 2023.pp. 1-2. (Year: 2023).*
Printout from https://discovery.lifemapsc.com/in-vivo-development/intermediate-mesoderm. Printed Nov. 2023 pp. 1-3. (Year: 2023).*
Wu et al. BBA-Molecular Cell Research 1866 (2019):971-977 (Year: 2019).*
Albert Q. Lam et al, "Rapid and Efficient Differentiation of Human Pluripotent Stem Cells into Intermediate Mesoderm That Forms Tubules Expressing Kidney Proximal Tubular Markers" Journal of the American Society of Nephrology vol. 25: 1211-1225, 2014.
International Search Report issued Feb. 11, 2019, in PCT/KR2018/010525 filed Sep. 7, 2018.
Written Opinion issued Feb. 11, 2019, in PCT/KR2018/010525 filed Sep. 7, 2018.
Grant of Patent mailed May 27, 2019, in KR Patent Application No. 10-2017-0114680.
Extended European Search Report issued Apr. 23, 2021 in European Patent Application No. 18854264.1, 13 pages.
Nathan Bucay, et al., "A Novel Approach for the Derivation of Putative Primordial Germ Cells and Sertoli Cells from Human Embryonic Stem Cells" Stem Cells, vol. 27, No. 1, XP055794701, Jan. 1, 2009, pp. 68-77 and cover page.
Ekaterina Shlush, et al., "In Vitro Generation of Sertoli-Like and Haploid Spermatid-Like Cells from Human Umbilical Cord Perivascular Cells" Stem Cell Research & Therapy, XP055794772, vol. 8, No. 1, Feb. 15, 2017, pp. 1-16.
Yosef Buganim, et al., "Direct Reprogramming of Fibroblasts into Embryonic Sertoli-like Cells by Defined Factors" Cell Stem Cell, vol. 11, No. 3, XP055669247, Sep. 7, 2012, pp. 373-386.
Ying Guo, et al., "Long-Term Culture and Significant Expansion of Human Sertoli Cells Whilst Maintaining Stable Global Phenotype and AKT and SMAD1/5 Activation" Cell Communication and Signaling, Biomed Central, London, GB, XP021220494, vol. 13, No. 1, Mar. 25, 2015, p. 1-13.

(Continued)

*Primary Examiner* — Marcia S Noble
(74) *Attorney, Agent, or Firm* — Oblon, McClelland, Maier & Neustadt, L.L.P.

(57) ABSTRACT

Provided are stem cells-induced Serotoli-like cells, methods of preparing the same, and uses thereof. Sertoli-like cells according to one embodiment can be differentiated from embryonic stem cells with excellent proliferative capacity, and thus, can be obtained in large quantities. Also, since the Sertoli-like cells secrete immunosuppressive substances and form immune privilege and induce anti-inflammatory functions, they can be used for development of the cell therapeutic agent.

6 Claims, 16 Drawing Sheets

Specification includes a Sequence Listing.

(56) References Cited

OTHER PUBLICATIONS

Liping Wen, et al., "Generation and Characteristics of Human Sertoli Cell Line Immortalized by Overexpression of human Telomerase" Oncotarget, XP055794700, Mar. 7, 2017, pp. 16553-16570.

Hidefumi Yoshioka, et al., "Mesonephric FGF Signaling is Associated with the Development of Sexually Indifferent Gonadal Primordium in Chick Embryos" Developmental Biology, Elsevier, Amsterdam, NL, vol. 280, No. 1, XP004781362, Apr. 1, 2005, pp. 150-161.

Dong-Won Seol, et al., "In Vitro Derivation of Functional Sertoli-Like Cells from Mouse Embryonic Stem Cells" Cell Transplantation, vol. 27, No. 10, XP055794589, Sep. 14, 2018, pp. 1523-1534.

Chenze Xu, et al., "Inducing Non-genetically Modified Induced Embryonic Sertoli Cells Derived From Embryonic Stem Cells with Recombinant Protein Factors" Frontiers in Cell and Developmental Biology, vol. 8, XP055794619, Jan. 25, 2021, pp. 1-14.

Daniel Rodriguez Gutierrez, et al., "A Human Gonadal Cell Model From Induced Pluripotent Stem Cells" Frontiers in Genetics, vol. 9, XP55794695, Oct. 24, 2018, pp. 1-14.

Chenze Xu, et al., "Mapping Molecular Pathways for Embryonic Sertoli Cells Derivation Based on Differentiation Model of Mouse Embryonic Stem Cells" Stem Cell Research & Therapy, vol. 11, No. 1, XP055794594, Feb. 26, 2020, pp. 1-18.

\* cited by examiner

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Oct4, forward primer

<400> SEQUENCE: 1
tgtggacctc aggttggact                                                       20

<210> SEQ ID NO 2
<211> LENGTH: 21
<212> TYPE: DNA
<213> ORGANISM: Artificial Sequence
<220> FEATURE:
<223> OTHER INFORMATION: Oct4 reverse primer

<400> SEQUENCE: 2
tttcatgtcc tgggactcct c                                                     21

<210> SEQ ID NO 3
<211> LENGTH: 20
<212> TYPE: DNA
<213> ORGANISM: Artificial Sequence
<220> FEATURE:
<223> OTHER INFORMATION: Pax2 forward primer

<400> SEQUENCE: 3
ctgtttccag cgcctctaac                                                       20

<210> SEQ ID NO 4
<211> LENGTH: 20
<212> TYPE: DNA
<213> ORGANISM: Artificial Sequence
<220> FEATURE:
<223> OTHER INFORMATION: Pax2 reverse primer

<400> SEQUENCE: 4
gacgctcaaa gactcgatcc                                                       20

<210> SEQ ID NO 5
<211> LENGTH: 20
<212> TYPE: DNA
<213> ORGANISM: Artificial Sequence
<220> FEATURE:
<223> OTHER INFORMATION: Osr1 forward primer

<400> SEQUENCE: 5
ttcgtttgca agttctgtgg                                                       20

<210> SEQ ID NO 6
<211> LENGTH: 20
<212> TYPE: DNA
<213> ORGANISM: Artificial Sequence
<220> FEATURE:
<223> OTHER INFORMATION: Osr1 reverse primer

<400> SEQUENCE: 6
tgtagcgtct tgtggacagc                                                       20

<210> SEQ ID NO 7
<211> LENGTH: 20
<212> TYPE: DNA
<213> ORGANISM: Artificial Sequence

```
<220> FEATURE:
<223> OTHER INFORMATION: Lhx1 forward primer

<400> SEQUENCE: 7
cagtgtcgcc aaagagaaca                                                   20

<210> SEQ ID NO 8
<211> LENGTH: 20
<212> TYPE: DNA
<213> ORGANISM: Artificial Sequence
<220> FEATURE:
<223> OTHER INFORMATION: Lhx1 reverse primer

<400> SEQUENCE: 8
tcaacgtctc cagttgcttg                                                   20

<210> SEQ ID NO 9
<211> LENGTH: 22
<212> TYPE: DNA
<213> ORGANISM: Artificial Sequence
<220> FEATURE:
<223> OTHER INFORMATION: Wt1 forward primer

<400> SEQUENCE: 9
ccagtgtaaa acttgtcagc ga                                                22

<210> SEQ ID NO 10
<211> LENGTH: 18
<212> TYPE: DNA
<213> ORGANISM: Artificial Sequence
<220> FEATURE:
<223> OTHER INFORMATION: Wt1 reverse primer

<400> SEQUENCE: 10
tgggatgctg gactgtct                                                     18

<210> SEQ ID NO 11
<211> LENGTH: 20
<212> TYPE: DNA
<213> ORGANISM: Artificial Sequence
<220> FEATURE:
<223> OTHER INFORMATION: Sox9 forward primer

<400> SEQUENCE: 11
cacaagaaag accaccccga                                                   20

<210> SEQ ID NO 12
<211> LENGTH: 20
<212> TYPE: DNA
<213> ORGANISM: Artificial Sequence
<220> FEATURE:
<223> OTHER INFORMATION: Sox9 reverse primer

<400> SEQUENCE: 12
ggaccctgag attgcccaga                                                   20

<210> SEQ ID NO 13
<211> LENGTH: 20
<212> TYPE: DNA
<213> ORGANISM: Artificial Sequence
<220> FEATURE:
<223> OTHER INFORMATION: Sf1 forward primer

<400> SEQUENCE: 13
agaagtttct gagagcccgc                                                   20
```

<210> SEQ ID NO 14
<211> LENGTH: 20
<212> TYPE: DNA
<213> ORGANISM: Artificial Sequence
<220> FEATURE:
<223> OTHER INFORMATION: Sf1 reverse primer

<400> SEQUENCE: 14
tacgaatagt ccatgcccgc                                                  20

<210> SEQ ID NO 15
<211> LENGTH: 16
<212> TYPE: DNA
<213> ORGANISM: Artificial Sequence
<220> FEATURE:
<223> OTHER INFORMATION: Gata4 forward primer

<400> SEQUENCE: 15
ctggccagga ctgccg                                                      16

<210> SEQ ID NO 16
<211> LENGTH: 20
<212> TYPE: DNA
<213> ORGANISM: Artificial Sequence
<220> FEATURE:
<223> OTHER INFORMATION: Gata4 reverse primer

<400> SEQUENCE: 16
ggttgctcca gaaatcgtgc                                                  20

<210> SEQ ID NO 17
<211> LENGTH: 20
<212> TYPE: DNA
<213> ORGANISM: Artificial Sequence
<220> FEATURE:
<223> OTHER INFORMATION: Fshr forward primer

<400> SEQUENCE: 17
aatccgtgga ggttttcgct                                                  20

<210> SEQ ID NO 18
<211> LENGTH: 23
<212> TYPE: DNA
<213> ORGANISM: Artificial Sequence
<220> FEATURE:
<223> OTHER INFORMATION: Fshr reverse primer

<400> SEQUENCE: 18
agcacaaatc tcagttcaat ggc                                              23

<210> SEQ ID NO 19
<211> LENGTH: 25
<212> TYPE: DNA
<213> ORGANISM: Artificial Sequence
<220> FEATURE:
<223> OTHER INFORMATION: Scf forward primer

<400> SEQUENCE: 19
gaagacacaa acttggatta tcact                                            25

<210> SEQ ID NO 20
<211> LENGTH: 20
<212> TYPE: DNA
<213> ORGANISM: Artificial Sequence
<220> FEATURE:
<223> OTHER INFORMATION: Scf reverse primer

```
<400> SEQUENCE: 20
catcccggcg acatagttga                                              20

<210> SEQ ID NO 21
<211> LENGTH: 20
<212> TYPE: DNA
<213> ORGANISM: Artificial Sequence
<220> FEATURE:
<223> OTHER INFORMATION: TGF-beta1 forward primer

<400> SEQUENCE: 21
ccgcaacaac gccatctatg                                              20

<210> SEQ ID NO 22
<211> LENGTH: 20
<212> TYPE: DNA
<213> ORGANISM: Artificial Sequence
<220> FEATURE:
<223> OTHER INFORMATION: TGF-beta1 reverse primer

<400> SEQUENCE: 22
tgccgtacaa ctccagtgac                                              20

<210> SEQ ID NO 23
<211> LENGTH: 20
<212> TYPE: DNA
<213> ORGANISM: Artificial Sequence
<220> FEATURE:
<223> OTHER INFORMATION: Transferrin forward primer

<400> SEQUENCE: 23
tcttctcggg cagttgtgtc                                              20

<210> SEQ ID NO 24
<211> LENGTH: 20
<212> TYPE: DNA
<213> ORGANISM: Artificial Sequence
<220> FEATURE:
<223> OTHER INFORMATION: Transferrin reverse primer

<400> SEQUENCE: 24
catgagaagg gatccgagcc                                              20

<210> SEQ ID NO 25
<211> LENGTH: 21
<212> TYPE: DNA
<213> ORGANISM: Artificial Sequence
<220> FEATURE:
<223> OTHER INFORMATION: IL-6 forward primer

<400> SEQUENCE: 25
agccagabtc cttcagagag a                                            21

<210> SEQ ID NO 26
<211> LENGTH: 20
<212> TYPE: DNA
<213> ORGANISM: Artificial Sequence
<220> FEATURE:
<223> OTHER INFORMATION: IL-6 reverse primer

<400> SEQUENCE: 26
tggtcttggt ccttagccac                                              20

<210> SEQ ID NO 27
```

```
<211> LENGTH: 20
<212> TYPE: DNA
<213> ORGANISM: Artificial Sequence
<220> FEATURE:
<223> OTHER INFORMATION: Fas-L forward primer

<400> SEQUENCE: 27
gaactgcgag aactccgtga                                                    20

<210> SEQ ID NO 28
<211> LENGTH: 20
<212> TYPE: DNA
<213> ORGANISM: Artificial Sequence
<220> FEATURE:
<223> OTHER INFORMATION: Fas-L reverse primer

<400> SEQUENCE: 28
actccagaga tcagagcggt                                                    20

<210> SEQ ID NO 29
<211> LENGTH: 19
<212> TYPE: DNA
<213> ORGANISM: Artificial Sequence
<220> FEATURE:
<223> OTHER INFORMATION: Clusterin forward primer

<400> SEQUENCE: 29
gggtgtactt gagcagagc                                                     19

<210> SEQ ID NO 30
<211> LENGTH: 22
<212> TYPE: DNA
<213> ORGANISM: Artificial Sequence
<220> FEATURE:
<223> OTHER INFORMATION: Clusterin reverse primer

<400> SEQUENCE: 30
tccttggaat ctggagtccg gt                                                 22
```

STEM CELL-DERIVED SERTOLI-LIKE CELL, PREPARATION METHOD THEREFOR, AND USE THEREOF

This application is a continuation-in-part of PCT/KR2018/010525, filed on Sep. 7, 2018, and claims the priority of Korean Patent Application No. 10-2017-0114680, filed on Sep. 7, 2017, the entirety of which is a reference to the present application.

TECHNICAL FIELD

The present invention relates to Sertoli-like cells (SLCs) induced from stem cells, a method of preparing the same, and a use thereof.

BACKGROUND ART

Cell therapeutic agent refers to a medication used for the treatment, diagnosis and prevention which are performed by proliferating or screening viable autologous, allogenic, or xenogenic cells in vitro to restore the function of cells and tissues. Cell therapeutic agent can be classified into somatic cell therapeutics and stem cell therapeutics, depending on the type of cell used and the degree of differentiation. Stem cell therapeutics can be classified into embryonic stem cell therapeutics and adult stem cell therapeutics. Stem cell therapeutic agent has attracted attention for the ideal reason that stem cells with self-proliferative and multipotent capability can help regenerate damaged cells to treat the disease of patients and ameliorate symptoms. However, research on stem cells has difficulty in ethical problems and securing the desired number of cells. Embryonic stem cells have superior performance to adult stem cells, but have negative aspects in terms of bioethics. In the case of adult stem cells, the collecting and isolation processes of stem cells cause pains in the donor, and the isolation efficiency of stem cells is low.

On the other hand, Sertoli cells (SCs) are cells present in male testes. SCs form tight junctions to form immune privileged sites in the testes, and secrete a substance that modulates the function of the immune cells and thus, by themselves, have an immune privileged character and anti-inflammatory function. Accordingly, SCs can be used as cell therapeutic agent. In addition, because SCs are not proliferated after puberty, it is very difficult to secure the desired number thereof through in-vitro culture. Therefore, recently, studies to obtain SCs using pluripotent stem cells or direct differentiation have been carried out by a small number of researchers without any fruitful results.

Therefore, there is a need for a method for differentiation from embryonic stem cells into cells with SCs function.

DESCRIPTION OF EMBODIMENTS

Technical Problem

One aspect provides a method of producing Sertoli-like cells from stem cells.

Another aspect provides a composition for differentiation of stem cells into Sertoli-like cells.

Another aspect provides Sertoli-like cells produced by the method.

Another aspect provides a cell therapeutic agent for treating autoimmune disease including Sertoli-like cells produced by the method.

Solution to Problem

One aspect provides a method of producing Sertoli-like cells (SLCs) from stem cells, the method including: inducing differentiation into SLC by culturing stem cells.

The method may include inducing differentiation into intermediate mesoderm (IM) by culturing stem cells.

In a specific embodiment, a method of producing Sertoli-like cells (SLCs) from stem cells includes: inducing differentiation into intermediate mesoderm (IM) by culturing stem cells in a medium containing a glycogen synthase kinase 3β (glycogen synthase kinase 3: GSK-3) inhibitor, a base fibroblast growth factor (bFGF), and a retinoic acid (RA); and inducing differentiation into SLC by culturing the induced IM in a medium containing bFGF, a fibroblast growth factor 9 (fibroblast growth factor 9: FGF9), prostaglandin D2 (PDG2), follicle-stimulating hormone (FSH), and a glial cell-induced neurotrophic factor (GDNF).

The term "stem cells" refers to totipotent cells capable of differentiating into all kinds of cells or pluripotent cells capable of differentiating into different types of cells. Stem cells are undifferentiated cells and can be differentiated into cells of a specific tissue. Stem cells may be embryonic stem cells (ESC), adult stem cells, or induced pluripotent stem cells (iPSC). The embryonic stem cells are cells that are obtained by culturing in vitro the inner cell mass that is extracted from the blastocyst embryonic just before the fertilized egg implants in the mother's uterus. The adult stem cells are undifferentiated cells present only in a small amount in each tissue of the body and replace dead cells or damaged tissues. The induced pluripotent stem cells (iPSC) refer to cells of which pluripotency is induced, like embryonic stem cells, by injecting differentiation-related genes into somatic cells that have undergone differentiation to return them to the cell stage before differentiation. The embryonic stem cells may be, for example, mouse embryonic stem cells derived from a mouse.

In this method, since stem cells having infinite proliferative capacity are differentiated into Sertoli-like cells, a large amount of Sertoli-like cells can be obtained by the above method.

The term "Sertoli-like cells (SLC)" expresses sertoli-cell markers and refers to cells that have the characteristic of SCs. In general, Sertoli cells are present in the testes of males and regulate the maintenance and function of germ cells. The Sertoli-cell marker may be Wt1, Sox9, Sf1, Gata4, Fshr, Scf, or a combination thereof.

The term "differentiation" refers to the process of changing the structure and shape of stem cells to specific cells. Specifically, a fertilized egg, which is a single cell and made by fertilization of sperm and egg, divides into several cells of the same shape through the division called egg-split. Then, the respective cells change into specialized structures that form various tissues or organs through division and growth. The cells with these specialized structures perform their respective functions. As described above, the differentiation refers to the process of changing into the structure and shape appropriate for each function. The differentiation may include naturally occurring differentiation and induced differentiation.

The method includes inducing differentiation to IM by culturing stem cells in a medium containing a GSK-3 inhibitor, bFGF, and RA.

The inducing of differentiation into the IM may include (a) culturing stem cells in a medium containing a GSK-3 inhibitor, and (b) additionally culturing after adding of bFGF and RA to the medium. The culturing period of the process (a) may be about 1 day to about 3 days, for example, about 2 days, and the culturing period of the process (b) may be about 2 days to about 5 days, for example, about 4 days. When the culturing period exceeds the above days, the medium may be replaced with new medium.

The medium in the process (a) may further include L-glutamine, antibiotics, or a combination thereof. The antibiotic may be, for example, but not limited to penicillin/streptomycin.

The method includes inducing of differentiation into SLC by culturing the induced IM in a medium containing bFGF, FGF9, PDG2, FSH, and GDNF.

The culturing period of the inducing of differentiation into the SLC may be about 5 days to about 7 days, for example, about 6 days.

In this method, the concentration of the GSK-3 inhibitor may be from about 1 µM to about 10 µM, for example, about 1 µM, about 3 µM, about 5 µM, about 7 µM, or about 10 µM. The concentration of bFGF may be from about 50 ng/ml to about 200 ng/ml, for example, about 50 ng/ml, about 75 ng/ml, about 100 ng/ml, about 150 ng/ml, or about 200 ng/ml. The concentration of RA may be from about 0.5 µM to about 1.5 µM, for example, about 0.5 µM, about 1.0 µM, or about 1.5 µM. The concentration of FGF9 may be from about 50 ng/ml to about 200 ng/ml, for example, about 50 ng/ml, about 75 ng/ml, about 100 ng/ml, about 150 ng/ml, or about 200 ng/ml. The concentration of PDG2 may be from about 250 ng/ml to about 750 ng/ml, for example, about 250 ng/ml, about 300 ng/ml, about 400 ng/ml, about 500 ng/ml, about 600 ng/ml, about 700 ng/ml, or about 750 ng/ml. The concentration of FSH may be from about 5 ng/ml to about 15 ng/ml, for example, about 5 ng/ml, about 10 ng/ml, or about 15 ng/ml. The concentration of GDNF may be from about 5 ng/ml to about 15 ng/ml, for example, about 5 ng/ml, about 10 ng/ml, or about 15 ng/ml.

The IM may express PAX2, LHX1, or a combination thereof.

The term "glycogen synthase kinase 3β" (Glycogen Synthase Kinase 3: GSK-3) refers to a small molecule that causes a change in the Wnt signaling pathway. In the method, since stem cells are cultured in a medium containing a GSK-3 inhibitor, stem cells, for example, embryonic stem cells may be induced into intermediate mesoderm.

The GSK-3 inhibitor may be commercially available, synthetic, or isolated from organisms. The GSK-3 inhibitor may include, but is not limited to, CHIR99021 (CT99021, CAS 252917-06-9).

The term "base fibroblast growth factor (bFGF)" refers to factors involved in angiogenesis, wound healing, embryonic development and various endocrine signaling pathways. bFGF may play an important role in the process of proliferation and differentiation of various cells and tissues.

The term "retinoic acid (RA)" refers to the metabolite of vitamin A (retinol). RA may act as a molecule for intercellular signaling.

The term "prostaglandin D2 (PDG2)" is prostaglandin that binds to receptors PTGDR (DP1) and CRTH2 (DP2). PDG2 may be found in large amounts in the brain and mast cells in mammalian organs.

The term "follicle-stimulating hormone (FSH)" is synthesized by gonadotropic hormone of the anterior pituitary, and may be a substance that controls the development, growth, reproductive processes, and the like of the body.

The term "glial cell-induced neurotrophic factor (GDNF)" is a protein encoded by the GDNF gene and may be involved in the survival of many types of neurons.

In this method, the medium used in the process of inducing differentiation may include any conventional medium that can be used for the culture of stem cells. In one or more embodiments, the medium may include at least one selected from Dulbecco's modified eagle medium (DMEM), Keratinocyte-serum-free medium (SFM), and Roswell Park Memorial Institute 1640 medium (RPMI 1640 medium).

In this method, the medium may be supplemented with an additive. Generally, the medium may include neutral buffers in isotonic solutions (such as phosphates and/or high concentration bicarbonates) and protein nutrients (for example, serums such as FBS, serum substitutes, albumin, or essential and non-essential amino acids such as glutamine). Furthermore, the medium may include lipids (fatty acids, cholesterol, HDL or LDL extracts of serum) and other components found in most preservative mediums of this kind (such as insulin or transferrin, nucleosides or nucleotides, pyruvate salts, sugar sources in any ionized form or salt, such as glucose, selenium, glucocorticoids such as hydrocortisone and/or reducing agents such as β-mercaptoethanol. In one embodiment, the medium may include insulin-transferrin-selenium (ITS).

The method may further include isolating or purifying the induced SLC.

The isolating or purifying refer to isolating, sorting, or purifying, and the isolating or purifying may include any method that divides the cells according to specific criteria in the art. For example, the isolating or purifying may include magentic-activated cell sorting (MACS), fluorescence-activated cell sorting (FACS), or chromatography. In one embodiment, the isolating or purifying may be isolating or purifying cells that are positive for Sertoli-cell markers. The term "positive" may refer to, regarding a cell marker, meaning that the marker is present in greater amounts, or in higher concentrations, compared to other cells. The term may also mean that the cell has the marker in an amount sufficient to signal a signal greater than the background value, for example, a signal from a cytometry device.

According to the method, Sertoli cells, which are present in male testis and do not proliferate after puberty and cannot be obtained through in vitro culture, can be induced from embryonic stem cells with infinite proliferative capacity, and thus it is possible to produce a large amount of Sertoli-like cells.

Another aspect provides a composition for differentiation of stem cells into SLC, the composition including: a composition for inducing differentiation of stem cells into IM, the composition comprising a GSK-3 inhibitor, bFGF, and RA; and a composition for inducing differentiation of IM into SLC, the composition comprising bFGF, FGF9, PDG2, FSH, and GDNF.

The composition may be a medium for cell culture. The composition may further include L-glutamine, antibiotics, Insulin-Transferrin-Selenium (ITS), or a combination thereof. Insulin is a peptide hormone secreted from β cells on the islet of Langerhans of pancreas. Transferrin is a type of β-globulin that binds to trivalent iron ions of two molecules absorbed in the serum, and is an iron transporter protein that supplies iron necessary for cell proliferation or hemoglobin production to the inside of cells through transferrin receptors. Selenium is a trace mineral that is essential for various functions in the body and is an antioxidant.

Another aspect provides Sertoli-like cells (SLC) produced by the method.

The SLCs may be obtained in vitro or in vivo by differentiating from stem cells. That is, the SLCs may be induced from stem cells.

The SLCs may express Sertoli-cell markers. In one embodiment, the Sertoli-cell marker may include Wt1, Sox9, Sf1, Gata4, Fshr, Scf, or a combination thereof. In addition, SLCs may not express Oct4, which is a pluripotent marker. Thus, the SLCs exhibit similar characteristics to mature or immature Sertoli cells that express sertoli cell markers.

The SLCs may form a tube-like structure during culturing. In one embodiment, when the SLCs are cultured in a medium on a protein complex (for example, Matrigel), the SLCs may form cell aggregates and form tube-like structures. In one embodiment, the Sertoli cells may produce a uniform hexagonal alignment.

The SLCs exhibit high phagocytosis activity as Sertoli cells.

The SLCs may be maintained in the basal region of the seminiferous tubule or testicles, such as Sertoli cells.

The SLCs may express genes related to immune regulation. Therefore, the SLCs may have the superior immunomodulatory ability and form immune privilege than other cells.

Like Sertoli cells, the SLCs do not proliferate after differentiation, and thus do not form carcinogenic or teratomas.

Therefore, the SLCs have a significant immunosuppressive function and anti-inflammatory function, thereby avoiding autoimmune and immune rejection reactions, and since they are induced from stem cells, they can be cultured in large quantities. Accordingly, SLCs may be useful for the treatment of disease requiring immunosuppressive effect, such as autoimmune disease, as cell therapeutic agent.

Another aspect provides a cell therapeutic agent or pharmaceutical composition for treating autoimmune disease including SLCs produced by the method.

Another aspect provides the use of SLCs for use in the manufacture of a cell therapeutic agent, pharmaceutical compositions, or formulations.

In addition, another aspect provides the use of SLCs or the cell populations thereof, or cultures, lysates, or extracts thereof for use in the manufacture of a medicament for use in the treatment or prevention of a disease, for example, autoimmune disease.

In addition, another aspect provides a method of treating or preventing a disease, for example, autoimmune disease, the method including administering SLCs or the cell populations thereof, or cultures, lysates, or extracts thereof of an effective ingredient to a subject in need.

SLCs and a method of producing SLCs are the same as described above.

The term "cell therapeutic agent" is cells and tissues prepared by isolating from a subject, culturing and special manipulations, and a medicine (US FDA regulation) used for the purpose of treatment, diagnosis, and prevention, that is, a medicine used for therapeutic, diagnostic and prophylactic purposes through a series of actions, such as proliferating and screening living autologous, allogeneic or heterologous cells in vitro or otherwise altering the biological characteristics of cells, to restore the function of cells or tissues.

The term "treatment" refers to any action that improves or benefits the condition of the disease by administration of the cell therapeutic agent or pharmaceutical composition.

The term "active ingredient" or "effective amount" refers to any amount of a composition used in the practice of the disclosure provided herein that is sufficient to ameliorate, inhibit, or prevent a disease, disorder, or condition, or one or more symptoms thereof.

In one or more embodiment, the culture, lysate or extract of SLCs may be used instead of SLCs. The culture, lysate, or extract may be a useful alternative when it is difficult to use the cell as it is, and because they contain components of the cell including proteins, may show biological activities similar to or equivalent to the original cell. The lysate or extract can be obtained using a commercially available cell lysis kit or extraction kit.

The cell therapeutic agent or pharmaceutical composition may be formulated into a pharmaceutical preparation in a unit dosage form suitable for administration in the body of a patient according to a conventional method in the pharmaceutical field, and the preparation may include dosages that are effective by one or several administrations. Formulations suitable for this purpose include parenteral preparations including injectables such as injectable ampoules, injectable agents such as infusion bags, sprays such as aerosol preparations, and the like. The injectable ampoule may be mixed with an injection solution immediately before use, and physiological saline, glucose, mannitol, and Ringer's solution may be used as the injection solution. The infusion bag may be made of polyvinyl chloride or polyethylene and may be those of Baxter, Becton Dickinson, Medcep, National Hospital Products, or Terumo.

The pharmaceutical preparations may include, in addition to the active ingredient, one or more conventional pharmaceutically acceptable inert carriers such as preservatives, analgesic agents, solubilizers or stabilizers in the case of injections, and excipients, lubricants or preservatives in the case of topical administration.

The cell therapeutic agent or pharmaceutical composition thus prepared according to the present disclosure may be administered with other stem cells used for transplantation and other uses or in the form of a mixture with such stem cells using administration methods commonly used in the art. In one or more embodiments, they may be engrafted or implanted directly into the lesion of the patient in need of treatment, or may be directly implanted or injected into the abdominal cavity. However, the present disclosure is not limited thereto. In addition, the administration may be both non-surgical administration using a catheter and surgical administration methods such as injection or transplantation after dissection of the lesion. In one embodiment, the non-surgical administration method using a catheter is preferable. In addition to parenteral administration according to a conventional method, for example, in addition to direct administration to the lesion, it is also possible to transplant by vascular infusion, which is a common method.

For the daily dosage of the SLCs, the SLCs may be administered in a single or divided doses of $1.0 \times 10^4$ to $1.0 \times 10^{10}$ cells/kg body weight, preferably $1.0 \times 10^5$ to $1.0 \times 10^9$ cells/kg body weight. However, it is to be understood that the actual dosage of the active ingredient should be determined in light of several relevant factors such as the disease to be treated, the severity of the disease, the route of administration, the patient's weight, age and gender. Accordingly, the dosage shall not limit the scope of the present disclosure in terms of any aspects.

The cell therapeutic agent or pharmaceutical composition may induce immunosuppression and anti-inflammatory function, may form immune privilege, and may be able to be transformed using a method known in the art. Accordingly, the cell therapeutic agent or pharmaceutical composition may be useful as cell therapy for treating autoimmune disease.

The autoimmune disease may include at least one selected from rheumatoid arthritis, osteoarthritis, Behcet's disease, autoimmune cytopenia, autoimmune myocarditis, atopic dermatitis, asthma, primary cirrhosis, dermatomyositis, Goodfitz syndrome, autoimmune meningitis, Sjogren's syndrome, systemic lupus erythematosus, Addison's disease, alopecia areata, ankylosing spondylitis, autoimmune hepatitis, autoimmune mumps, Crohn's disease, diabetic disease, dystrophic epidermolysis bullosa, epididymitis, glomerulonephritis, Graves' disease, Guillain-Barré syndrome, Hashimoto's disease, hemolytic anemia, systemic lupus erythematosus, multiple sclerosis, myasthenia gravis, pemphigus vulgaris, psoriasis, sarcoidosis, scleroderma, seronegative spondyloarthropathy, pernicious anemia, scleroderma, mitochondrial related syndrome, and inflammatory bowel disease.

The SLCs can be used in various types of treatment protocols in which the tissues or organs of the body are enriched, treated or replaced by engraftment, transplantation or infusion of the desired cell population.

The cell therapeutic agent and the pharmaceutical composition may be used unfrozen, or frozen for future use. When there is a need to be frozen, standard cryopreservatives (for example, DMSO, glycerol, Epilife® cell freezing medium (Cascade Biologics)) may be added to the cell population prior to freezing.

The term "administration" refers to introducing the cell therapeutic agent of the present disclosure to a patient in any suitable manner and includes the implantation of differentiated cells. The route of administration of the cell therapeutic agent or pharmaceutical composition of the present disclosure may be administered through various routes as long as the target tissue can be reached. A cell of the composition according to an embodiment or at least a portion of cellular components may be administered by any suitable route for delivery to a desired location within a living subject. Cell survival after subject administration may last several hours, for example, 24 hours to several days, or to several years.

Administration of the cell therapeutic agent or pharmaceutical composition is applicable to any animal, and the animal may include humans and primates, and domestic animals such as cattle, pigs, sheep, horses, dogs, mice, rats, and cats.

Another aspect provides a health functional food composition for preventing or ameliorating autoimmune disease, including SLCs, or the culture, lysate, or extract thereof.

The health food composition may be used with other foods or food ingredients in addition to the SLCs, and may be appropriately used according to conventional methods. The mixed amount of the active ingredient may be determined suitably according to the purpose of use (prevention, health or therapeutic treatment). In general, in the manufacture of a health functional food, the composition of the present disclosure may be added in an amount of 15 parts by weight or less based on the raw material. There is no particular limitation on the kind of the health food.

The inventors have confirmed that SLCs secrete immunosuppressive agents to form immune privilege and induce anti-inflammatory functions, and thus compositions including the same may be useful for the treatment, prevention, or improvement of autoimmune disease.

Advantageous Effects of Disclosure

SLCs according to one embodiment can be obtained in large quantities because they can be differentiated from embryonic stem cells with excellent proliferative capacity. Also, since SLCs secrete immunosuppressive substances and induce anti-inflammatory functions, they can be used for the development of cell therapeutic agent for autoimmune diseases.

MODE OF DISCLOSURE

Hereinafter, the present disclosure will be described in more detail with reference to Examples. However, these examples are intended to illustrate the present disclosure and the scope of the present disclosure is not limited to these examples.

Example 1. Specification from Mouse Embryonic Stem Cells (ESC) to Intermediate Mesoderm (IM)

1.1 Storage of Mouse ESC (mESCs)

mESC strain (karyotype: XY) was derived from C57BL/6 substrain mice and GFP-expressing transgenic mice [C57BL/6-Tg (CAG-EGFP), Japan SLC, Inc., Shuzuoka, Japan], and the mouse embryonic fibroblasts (MEFs; CF1 strain, Jackson Laboratory, Los GoTos, Calif.) were cultured as feeder cells. The cells were stored in a culture medium consisting of 80% (v/v) DMEM high glucose (HyClone, Logan, UT) containing 20% (v/v) mESC, SR (Gibco-BRL, Frankin Lakes, NJ), 1% (v/v) NEAA (Gibco-BRL), 0.1% (v/v) β-mercaptoethanol (Gibco-BRL), 100 U/ml LIF (ES-GRO, Chemicon, Temecula, CA), in an incubator at a temperature of an 37° C. in a 5% wet $CO_2$. For passage, mESC was treated with 0.05% trypsin-EDTA (TE; HyClone) for 3 minutes, removed from the dish and divided into new MEF-seed dishes every 3 to 4 days. mESC culture medium was exchanged daily.

1.2. Differentiation of mESC into IM and Confirmation of the Same

Undifferentiated mESCs stored as described above were seeded on an eltrex (Gibco-BRL)-coated plate at a density of $6\pm10^4$ cells/cm² in an EC cell culture medium. After overnight incubation, the cells were treated with Advanced RPMI (A-RPMI 1640; Gibco-BRL) supplemented with 100× L-GlutaMAX (L-glu; Gibco-BRL) and 1% penicillin/streptomycin (P/S; Gibco-BRL) and 5 μM CHIR99021 (glycogen synthase kinase-3β inhibitor; Stemgent, Lexington, MA), for 36-48 hours (for about 2 days). Thereafter, the cells were induced into IM by treatment with 100 ng/ml bFGF (Peprotech, Rocky Hill, NJ) and 1 μM retinoic acid (RA; Sigma, St. Louis, MO) for about 4 days. After about 2 days, the medium was replaced.

Figure 1:
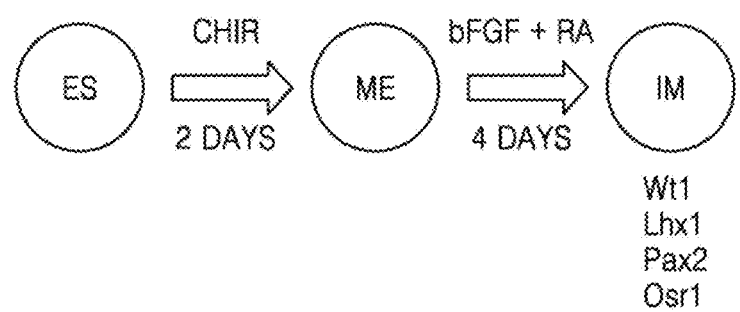
FIG. 1 illustrates a simplified diagram showing the method of specification from embryonic stem cells (ES) into intermediate mesoderm (IM) via mesendodem (ME) (CHIR: CHIR99021).

FIG. 1 illustrates a simplified diagram showing the method of specification from embryonic stem cells (ES) into intermediate mesoderm (IM) via mesendodem (ME).

Figure 2:
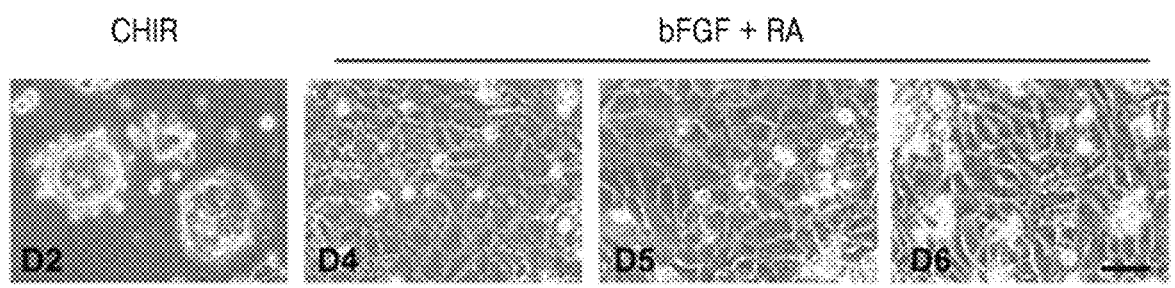
FIG. 2 shows a day-2 phase change image (D2) of mESC treated with CHIR, and day-4, 5, and 6 phase change images (D4, D5, D6) of mESC treated with bFGF and RA (CHIR: CHIR99021).

FIG. 2 shows a day-2 (D2) phase change image of mESC treated with CHIR, and day-4, 5, and 6 (D4, D5, D6) phase change images of mESC treated with bFGF and RA (CHIR: CHIR99021).

As shown in FIG. 2, on day 2 after mESC was treated with CHIR99021 (D2), it was confirmed that the shape of the cell clusters did not change. In addition, after treatment with bFGF and RA for 4 days, 5 days, and 6 days (D4, D5, D6), it was confirmed that the cells changed and proliferated and the number of the attached cells was increased.

When the specification was progressed from mESC to IM, the expression of IM marker genes Pax2, Osr1, Lhx2 and Wt1 and the expression of pluripotent marker gene Oct4 were confirmed by RT-PCR analysis. For RT-PCR, total RNA was isolated from cells at each step using TRIzol Reagent (Invitrogen) and quantified using NANODROP 2000 UV/Ms Spectrophotometer (Thermo Scientific, Waltham, MA). RT-PCR was performed using First Strand cDNA Synthesis kit (Takara Bio, Shiga, Japan) and AccuPower PCR premix (Bioneer, Deajeon, Korea) according to the manufacturers instructions. All PCR products were isolated by 2% agarose gel electrophoresis. Primer sets used are shown in Table 1 below.

TABLE 1

| gene | Foward direction primer | Reverse primer |
| --- | --- | --- |
| Oct4 | 5'-TGTGGACCTCAGGTTGGA CT-3' (SEQ ID NO: 1) | 5'-TTTCATGTCCTGGGAC TCCTC-3' (SEQ ID NO: 2) |
| Pax2 | 5'-CTGTTTCCAGCGCCTCTA AC-3' (SEQ ID NO: 3) | 5'-GACGCTCAAAGACTCG ATCC-3' (SEQ ID NO: 4) |
| Osr1 | 5'-TTCGTTTGCAAGTTCTGT GG-3' (SEQ ID NO: 5) | 5'-TGTAGCGTCTTGTGGA CAGC-3' (SEQ ID NO: 6) |
| Lhx1 | 5'-CAGTGTCGCCAAAGAGA ACA-3' (SEQ ID NO: 7) | 5'-TCAACGTCTCCAGTTG CTTG-3' (SEQ ID NO: 8) |
| Wt1 | 5'-CCAGTGTAAAACTTGTCA GCGA-3' (SEQ ID NO: 9) | 5'-TGGGATGCTGGACTGT CT-3' (SEQ ID NO: 10) |

Figure 3:
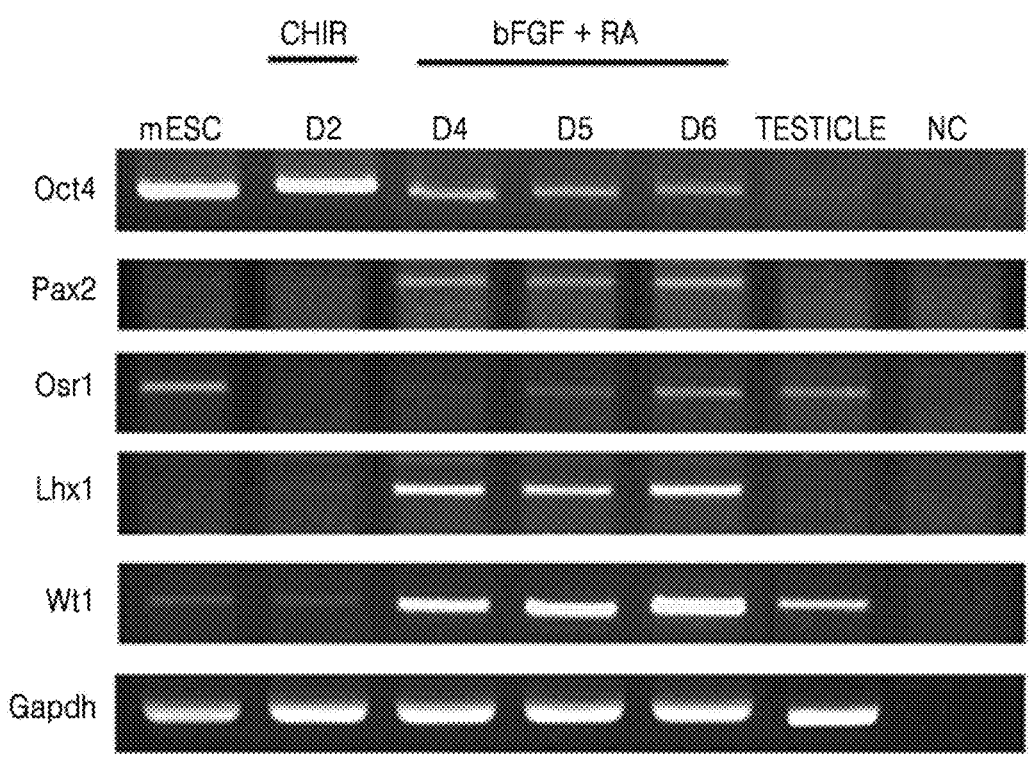
FIG. 3 shows the results of RT-PCR confirming mRNA expression levels of Oct4, Pax2, Osr1, Lhx2, and Wt1 on days 2, 4, 5, and 6 (D2, D4, D5, and D6) while mESC was induced into IM.
Figure 4:
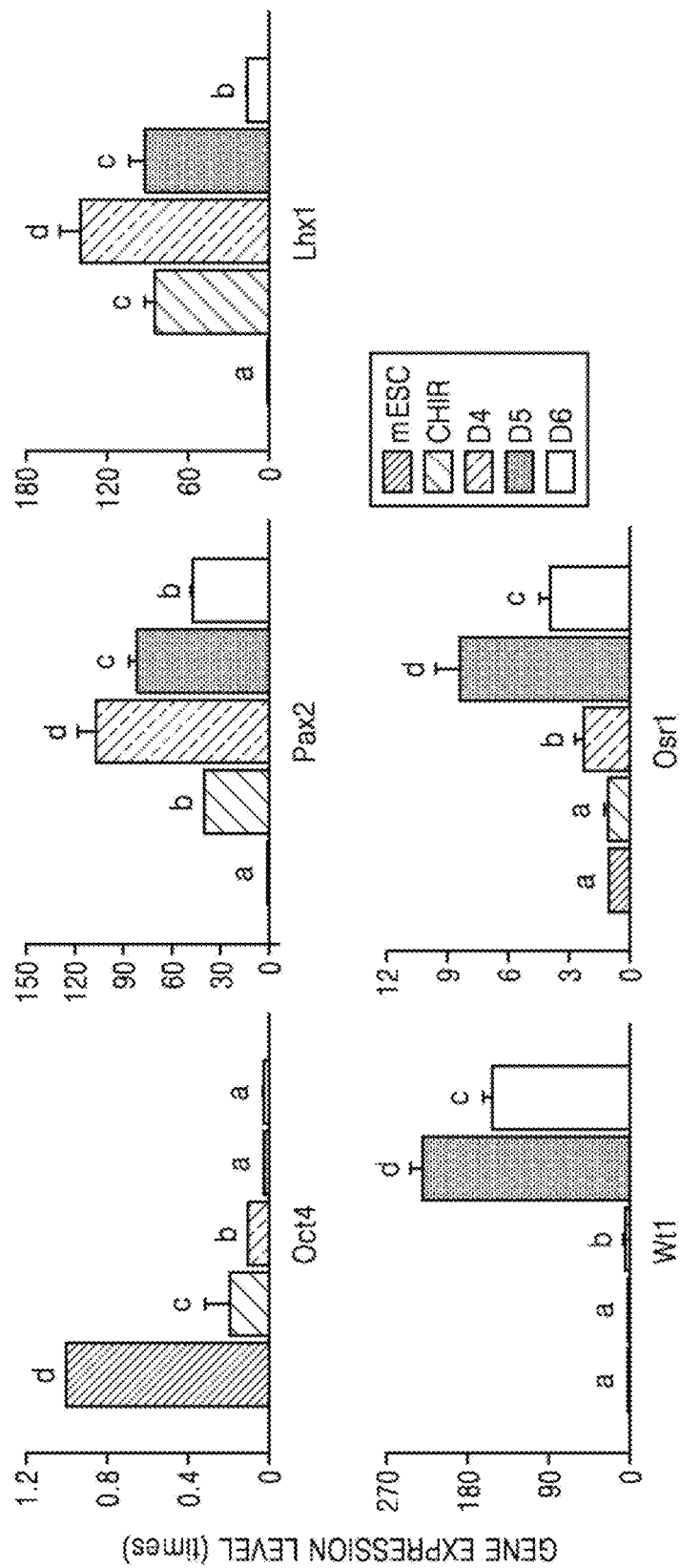
FIG. 4 shows the results of real time-PCR confirming mRNA expression levels of Oc4, Pax2, Lhx1, Wt1, and Osr1 on days 2, 4, 5, and 6 (D2, D4, D5, and D6) while mESC was induced into IM.

FIGS. 3 and 4 show the results of RT-PCR and real time PCR confirming mRNA expression levels of Oct4, Pax2, Osr1, Lhx2, and Wt1 on days 2, 4, 5, and 6 (D2, D4, D5, and D6) while mESC was induced into IM. As shown in FIGS. 3 and 4, while mESC was specified into IM, no expression of IM marker was detected in cells cultured with CHIR99021 for 2 days. However, after 2 days of treatment with bFGF and RA, expressions of Pax2, Lhx1 and Wt1 were detected, and Osr1 was not observed on day 2 of treatment with bFGF and RA (D4). After 4 days of treatment with bFGF and RA (D6), it was confirmed that all IM markers were expressed in the cells.

In addition, the expression of PAX2 and LHX1, which are IM markers, in mESC-induced IM were confirmed by immunofluorescent staining. Specifically, the analyte cells were fixed with 4% paraformaldehyde (PFA, Biosesang, Gyeonggi-do, Korea) in PBS at a temperature of 4° C. and permeated for 5 minutes with 0.1% Triton X-100 (Sigma) in PBS. Then, the cells were blocked with a blocking solution (DAKO North America Inc., Carpinteria, Calif.) at room temperature for 1 hour and incubated with primary antibody overnight at a temperature of 4° C. Secondary antibodies were incubated for 1 hour at room temperature, and the antibodies and dilutions used herein are as follows: LHX1 (1:100; Santa Cruz), PAX2 (1:100; Thermo Scientific), GATA4 (1:100; SantaCruz), and FSHR (1:100, Santa Cruz). Secondary antibodies used were as follows: Alexa-488, Alexa-594, and Alexa-488 (1:200, Life Technologies). Primary antibodies used for immunohistochemistry were as follows: GFP (1:100; Abcam, Boston, Mass.) and GATA4 (1:100; Santa Cruz). Secondary antibodies used were as follows: Alexa-488 and Alexa-594 (1:100, Life Technologies). After all treatments immunofluorescence images were obtained using a confocal microscope (Carl Zeiss LSM 880, Oberkochen, Germany).

Figure 5:
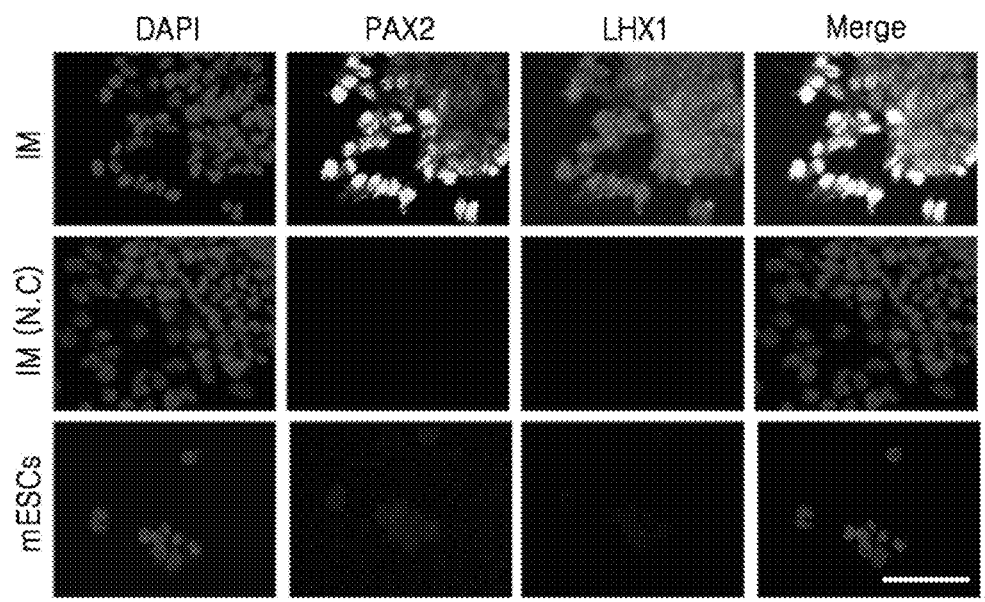
FIG. 5 shows the results of immunofluorescence staining for IM markers PAX2 and LHX1 in mESC-induced IM; Scale bar of 50 μm.

FIG. 5 shows the results of immunofluorescence staining for IM markers PAX2 and LHX1 in mESC-induced IM.

As shown in FIG. 5, all IM markers were detected in the mESC-induced IM. Therefore, it was confirmed that the above-described treatment conditions can induce an IM exhibiting IM characteristics from mESC.

Example 2. Differentiation from mESC-Induced IM to Sertoli-Like Cells (SLC)

In order to differentiate the mESC-induced IM to SLC as in Example 1, the cells at the stage of IM were treated, for about 6 days, with 100 ng/ml bFGF, 100 ng/ml FGF-9 (Peprotech), 500 ng/ml prostaglandin D2 (PGD2, Santa Cruz Biotechnology, Dallas, TX), 10 ng/ml glia cell line-induced neurotrophic factor (GDNF; R&D, Minneapolis, MN), 10 ng/ml follicle stimulating hormone (FSH; Sigma), and 100×ITS (insulin-transferrin-selenium; Invitrogen, Grand Island, NY). Medium was exchanged every 2 days. The cell morphology was confirmed 6 to 7 days after the deriving.

Figure 6:
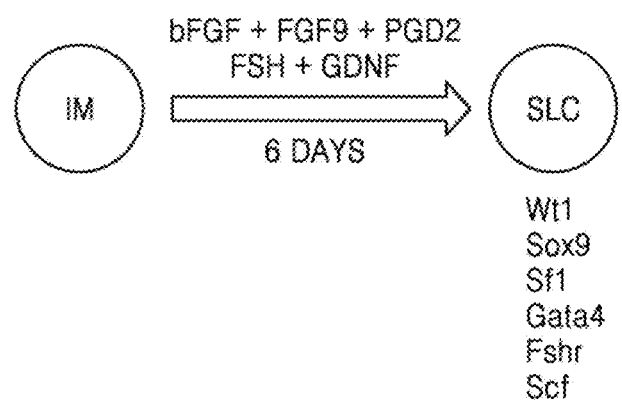
FIG. 6 shows a schematic view illustrating a method of differentiating mESC-induced IM into SLC.

FIG. 6 shows a schematic view illustrating a method of differentiating mESC-induced IM into SLC.

Figure 7:
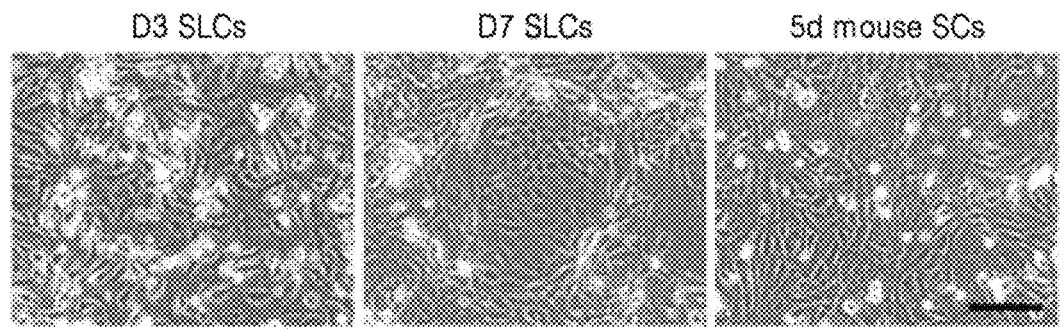
FIG. 7 shows phase change images of SLCs 3 days after differentiation from IM (D3 SLCs) and 7 days after differentiation from IM (D7 SLCs), and 5-day old mouse SCs, which are immature mouse SCs.

FIG. 7 shows phase change images of SLCs 3 days after differentiation from IM (D3 SLCs) and 7 days after differentiation from IM (D7 SLCs), and 5-day old mouse SCs, which are immature mouse SCs.

As shown in FIG. 7, after differentiation of IM to SLC, it was confirmed that, like immature mouse Sertoli cells, induced SLC formed a cord-like structure.

In addition, the experiment was performed as follows to determine whether the induced SLC as described above can easily form a tube-like structure. Immature Sertoli cells obtained from 5 day-old mouse (5 d mouse SCs) and SLC induced from ESCs were cultured for about 48 hours in a differentiation medium on matrigel (the same as the medium for SLC differentiation). As a control, cells cultured in 10% FBS were used. The morphologies of the test group and the control were used to compare the cord-like structures, and the results thereof are shown in FIG. 7.

Figure 8:
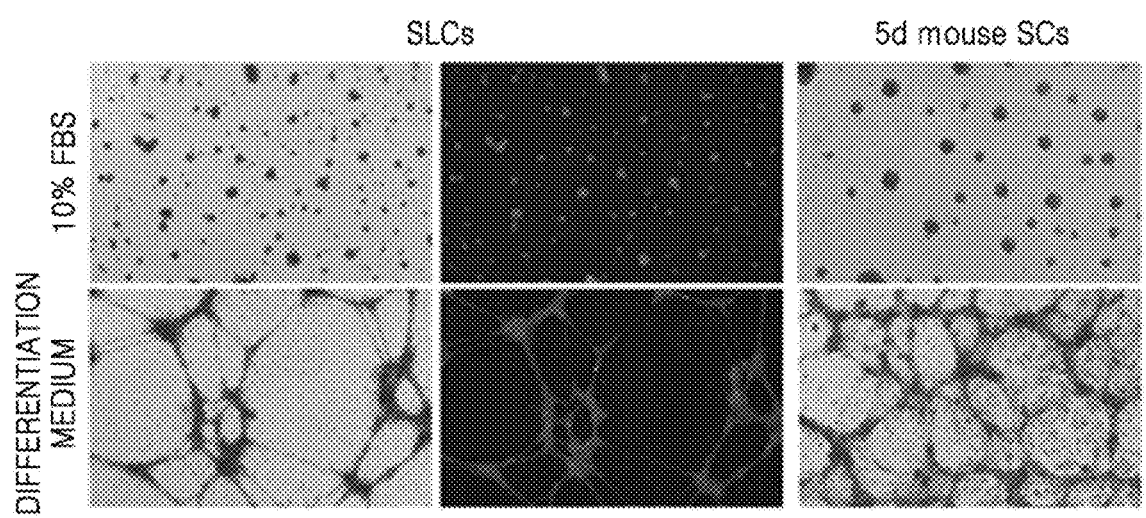
FIG. 8 shows images of SCs obtained from 5-day old mouse (5 d mouse SCs) and ESC-induced SLCs which were cultured in 10% FBS and a differentiation medium, the images confirming the morphology thereof.

As shown in FIG. 8, it was confirmed that, when cultured in the differentiation medium on Matrigel, cells, like 5 day-old mouse Sertoli cells, formed cell aggregates after about 48 hours and formed a 3D hollow cord-like structure. The 3D cord-like structure was hollow, like a tube, and produced a very uniform hexagonal alignment in the Matrigel. On the other hand, when cultured in 10% FBS, it was confirmed that the cells did not form the hollow cord-like structure.

Therefore, it was confirmed that, when cells were cultured in SLC differentiation medium on Matrigel, a web-like structure was formed. Since the web-like structure indicates the possibility of tube formation, it was confirmed that SLC induced from IM can easily form the tube-like structure.

In addition, in order to confirm whether SLC induced from IM has the characteristics of Sertoli cells, mRNA levels of Wt1, Sox9, Sf1, Gata4, Fshr, and Scf genes, which are the markers of Sertoli cells, and Oct4 gene, which is a pluripotency marker gene, were identified by RT-PCR and real time PCR. Information on the primer sets used for RT-PCR and real time PCR is shown in Table 2 below.

TABLE 2

| Gene | Forward primer | Reverse primer |
|------|----------------|----------------|
| Sox9 | 5'-CACAAGAAAGACCACC CCGA-3' (SEQ ID NO: 11) | 5'-GGACCCTGAGATTGCCC AGA-3' (SEQ ID NO: 12) |
| Sf1 | 5'-AGAAGTTTCTGAGAGC CCGC-3' (SEQ ID NO: 13) | 5'-TACGAATAGTCCATGCCC GC-3' (SEQ ID NO: 14) |
| Gata4 | 5'-CTGGCCAGGACTGCCG-3' (SEQ ID NO: 15) | 5'-GGTTGCTCCAGAAATCGT GC-3' (SEQ ID NO: 16) |
| Fshr | 5'-AATCCGTGGAGGTTT TCGCT-3' (SEQ ID NO: 17) | 5'-AGCACAAATCTCAGTTCA ATGGC-3' (SEQ ID NO: 18) |
| Scf | 5'-GAAGACACAAACTTGG ATTATCACT-3' (SEQ ID NO: 19) | 5'-CATCCCGGCGACATAGTT GA-3' (SEQ ID NO: 20) |

Figure 9:
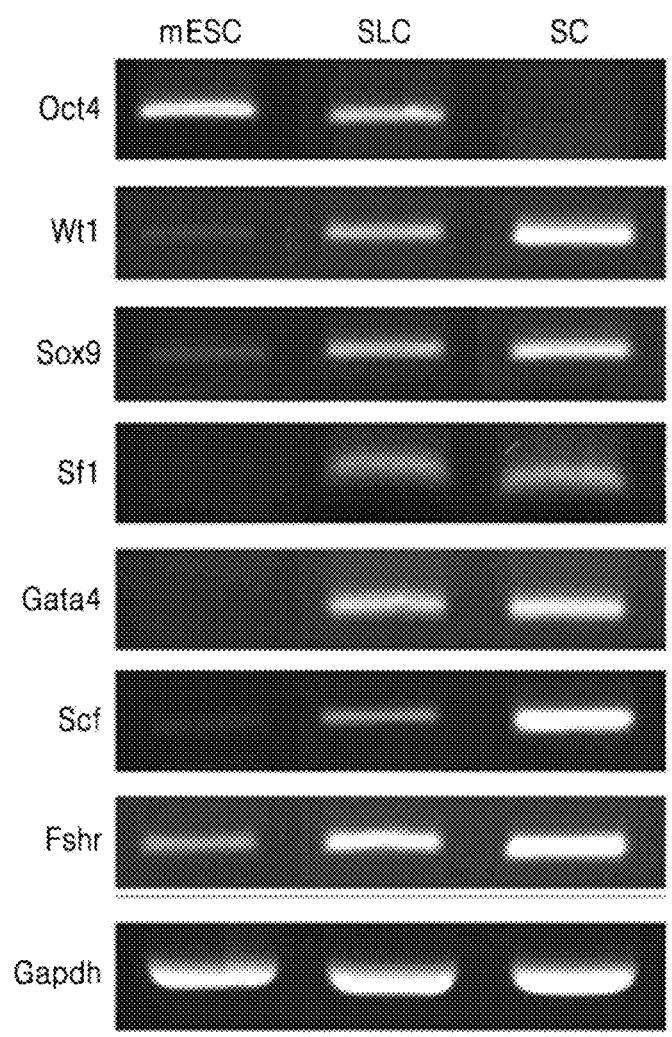
FIG. 9 shows the results of RT-PCR confirming mRNA expression levels of Oct4, Wt1, Sox9, Sf1, Gata4, Fshr, and Scf in mESC, induced SLC, and SCs.
Figure 10:
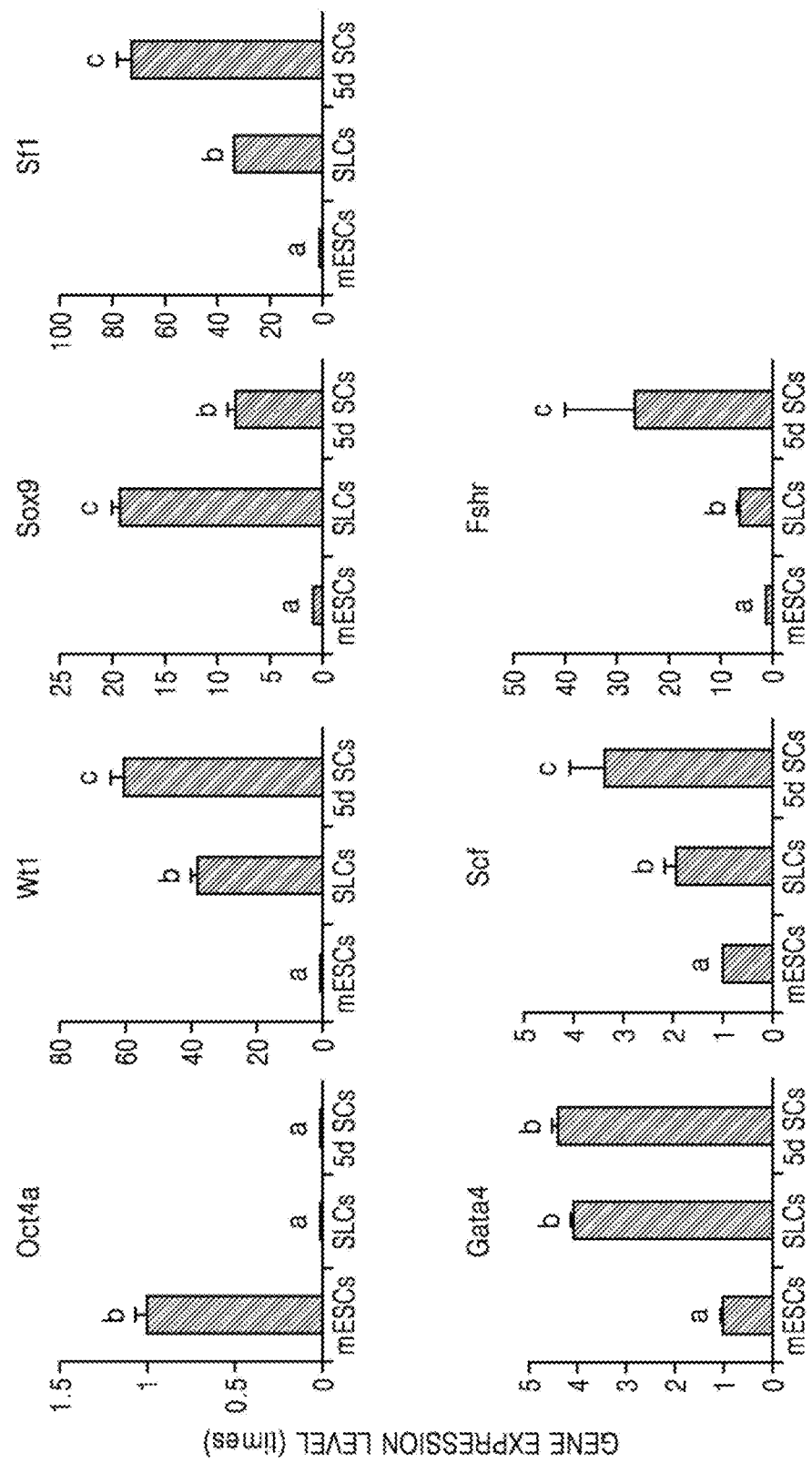
FIG. 10 is the graph showing the results of real time PCR confirming mRNA expression levels of Oct4, Wt1, Sox9, Sf1, Gata4, Fshr, and Scf in mESC, induced SLC, and SCs.

FIGS. 9 and 10 are the graphs showing the results of RT-PCR and real time PCR confirming mRNA expression levels of Oct4, Wt1, Sox9, Sf1, Gata4, Fshr, and Scf in mES cells, induced SLC, and SCs. As shown in FIGS. 9 and 10, sertoli cell markers were not expressed in mES, whereas expressions of sertoli cell markers Wt1, Sox9, Sf1, Gata4, Fshr and Scf in induced SLC were at the level similar to those of Sertoli cells.

Therefore, since the SLC induced from IM expresses sertoli cell markers, it was confirmed that the cells were SLC having the characteristics of Sertoli cells.

In addition, the expression of serotoli cell markers GATA4 and FSHR in induced SLC was confirmed by immunofluorescent staining. As a control, 5 day-old mouse Sertoli cells (5 d mouse SCs) were used.

Figure 11:
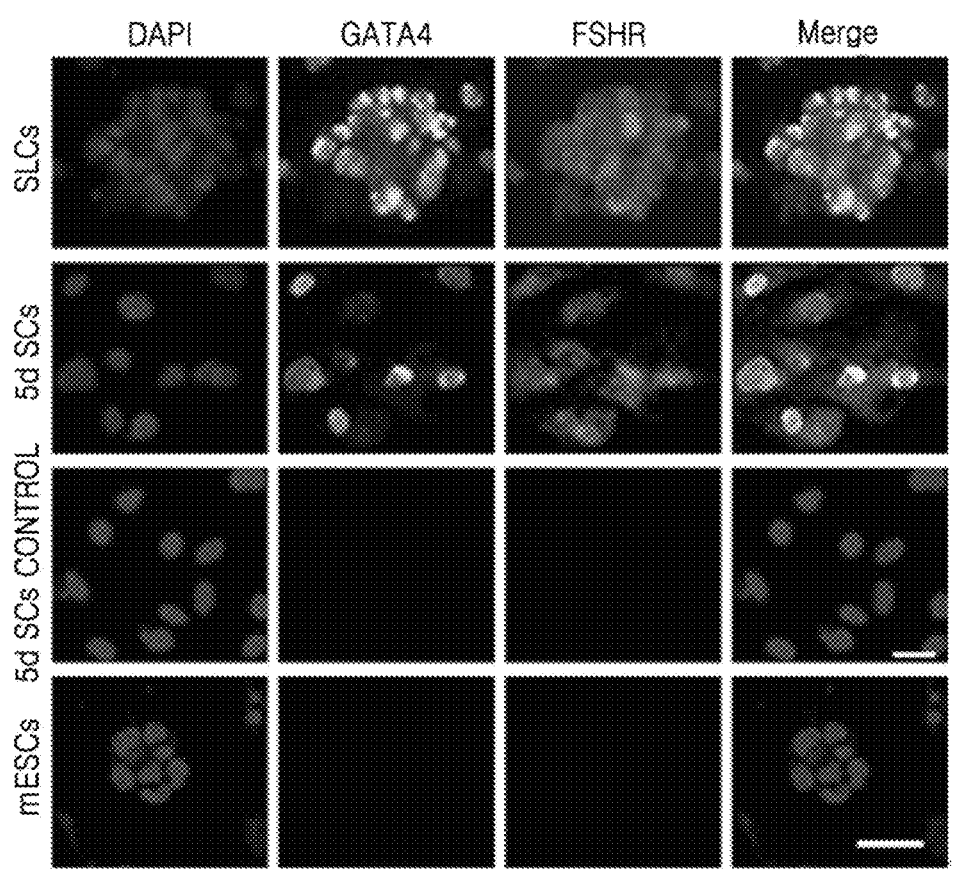
FIG. 11 shows immunofluorescence staining results for SC markers GATA4 and FSHR in SLC induced from IM; Scale bar of 50 μm.

FIG. 11 shows immunofluorescence staining results for SC markers GATA4 and FSHR in SLC induced from IM.

As shown in FIG. 11, since the sertoli cell markers were detected in SLC induced from IM, it was confirmed that SLC induced from IM exhibited the characteristics of the Sertoli cells.

Therefore, it was confirmed that ESC-induced SLC was differentiated to SLC under the above conditions and that characteristics of SLC were similar to those of immature Sertoli cells obtained from 5 day-old mouse.

Example 3. Isolation, Purification and Characterization Identification of Sertoli Cells of Induced SLC 3.1 Isolation and Purification of Induced SLC As shown in FIG. 11, the weak expression of Oct4 mRNA, which is a pluripotent marker in SLC, indicates that ESC that is undifferentiated or SLC that is in differentiation remains in differentiated SLC. Therefore, in order to isolate and purify differentiated SLC from the culture, MACS using an antibody against FSHR, which is a testicle sertoli cell marker, was performed.

Specifically, differentiated SLC $1 \times 10^7$, was trypsinized, collected, and the anti-FSHR-biotin antibody (1:20, Bioss, Woburn, MA) was Incubated in 100 µl MACS solution (Miltenyi Biotec, Gladbach) for 30 minutes at room temperature. Unbound anti-FSHR-biotin antibody was washed and removed by centrifugation twice at 300×g for 10 min after the addition of 1 ml to 2 ml of buffer. Cell pellets were resuspended in 80 µl buffer, and 20 µl anti-biotin microbeads (UltraPure, Miltenyi Biotec) were added thereto and mixed well, followed by incubation at a temperature of 4° C. for 15 minutes. Cells were then washed with 2 ml 0.5% BSA (Sigma) in PBS buffer and centrifuged at 300×g for 10 minutes to remove excess beads from the solution. The wash solution is then processed and, according to the manufacturer's guidelines, the pellets were resuspended in 500 µl buffer at maximum column capacity and the suspension was placed on a pretreated LD column (Miltenyi Biotec) mounted on a MACSMidi magentic cell isolator (Miltenyl Biotec). The column was washed twice with 2 ml buffer to remove unmarked cells. After removing the column from the magentic isolator, the isolated cells were eluted with 1 ml buffer to collect purified, isolated SLC.

3.2 Characterization of Cells after Isolation and Purification of Induced SLC

Figure 12:
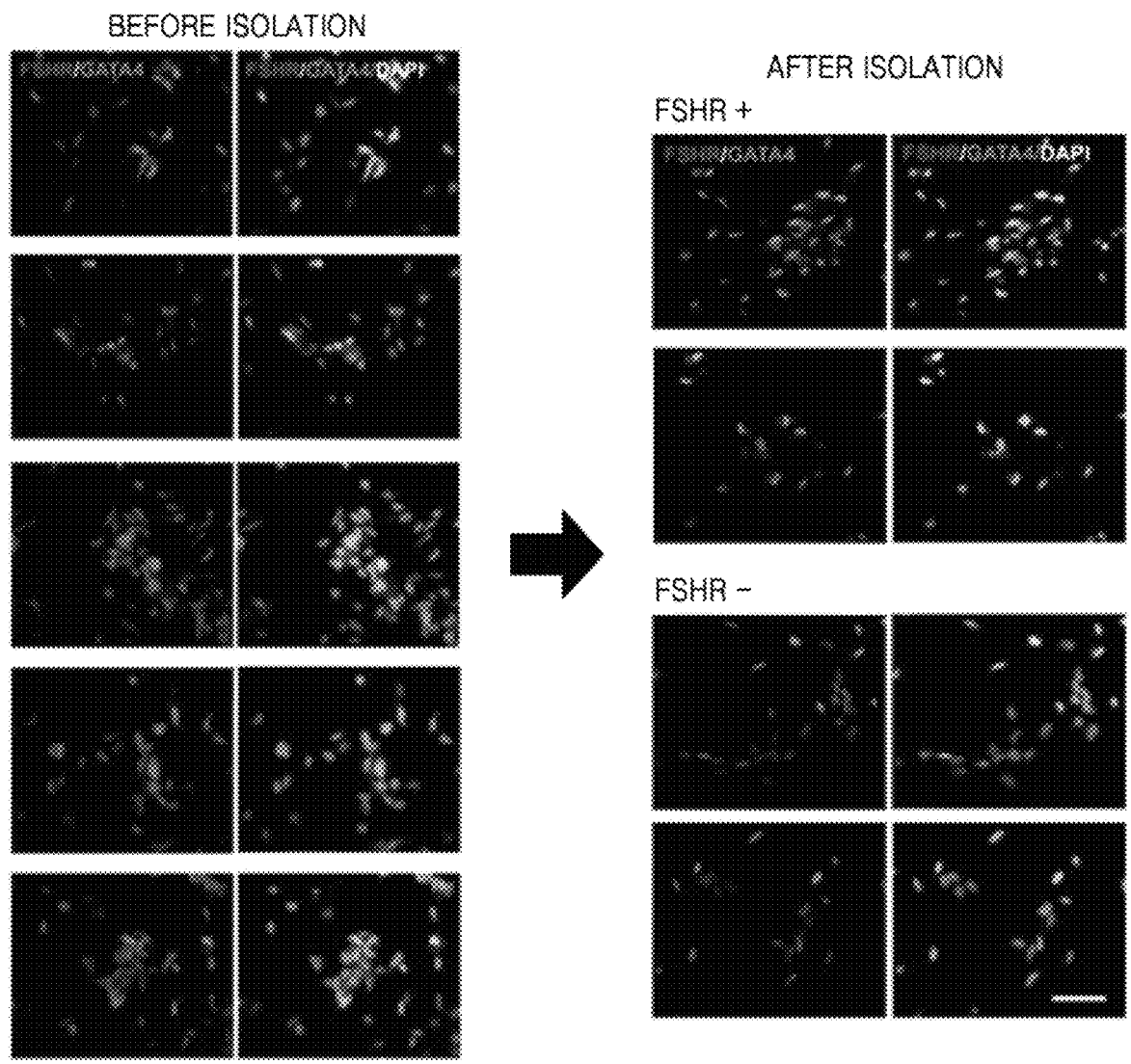
FIG. 12 shows an image showing the results of immunostaining of SLC with respect to FSHR and GATA4 before purification, isolation and after isolation; FSHR+: FSHR positive; FSHR−: FSHR negative.

In order to confirm that the induced SLC was purified and isolated by the above method, immunostaining was performed on the sertoli cell markers FSHR and GATA4. FIG. 12 shows an image showing the results of immunostaining of SLC before and after purification and isolation with FSHR and GATA4.

As shown in FIG. 12, it was confirmed that the ratio of FSHR and GATA4-double positive SLC increased after isolation as compared with before isolation and purification.

In addition, flow cytometric analysis was further performed as follows. SLC before and after isolation were collected and fixed with 4% paraformaldehyde for 4 minutes at room temperature. After washing, the cells were permeated with cooled 90% methanol for 10 minutes. Cells were then blocked with 0.5% BSA (Sigma)/PBS for 30 minutes at room temperature and cultured with primary antibody. To assess the efficiency of FSHR MACS, cells were incubated with anti-rabbit FSHR antibody (Santa Cruz) and anti-mouse GATA4 antibody at a temperature of 4° C. for 1 hour. Secondary antibodies were detected by incubation using APC-conjugated (Life technology) and PE-conjugated antibodies at a temperature of 4° C. for 1 hour. Control cells were not treated with the primary antibody. Cells were stored on ice in the dark condition until analysis, using Becton DicKinson FACS IV Calibur (Becton Dickinson, San Jose, Calif.). At least 5,000 or 10,000 events were collected for each sample.

Figure 13:
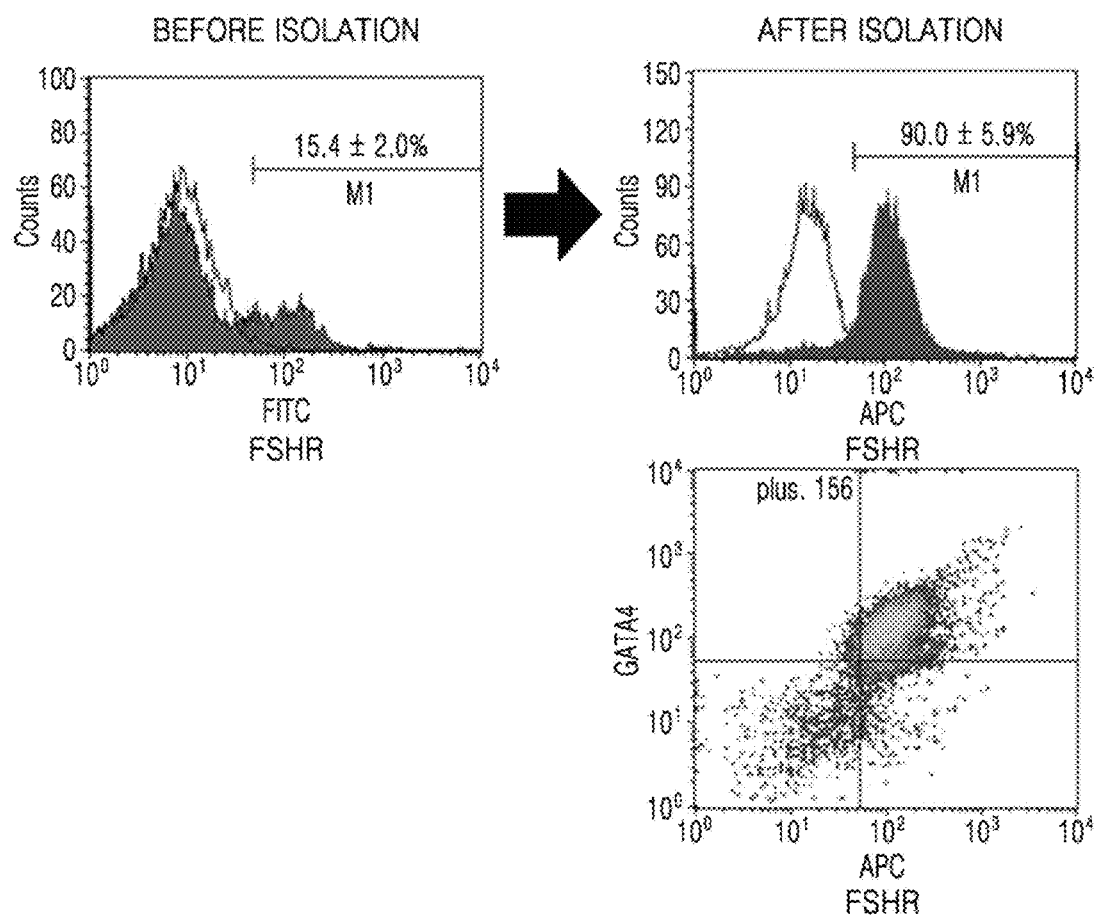
FIG. 13 shows a graph of the flow cytometry results before and after isolation.

FIG. 13 shows a graph of the flow cytometry results before and after isolation.

As shown in FIG. 13, it was confirmed that the FSHR-positive SLC ratio (90.0±5.9%) after isolation was significantly greater than the FSHR-positive SLC ratio (15.4±2.0%) before isolation. In addition, it was confirmed that most of the detected cells were FSHR and GATA4-double positive SLC.

In addition, mRNA expression levels of Oct4, Wt1, Sox9, Gata4, and Fshr genes in FSHR-positive SLC and FSHR-negative SLC were confirmed by real time PCR and RT-PCR. Specifically, real time PCR was performed in such a manner that total RNA was extracted from each cell using the method as described above, and for quantification of gene expression levels, in Bio-Rad CFX96™ real-time PCR, iQ™\SYBR Green supermix (Bio-Rad Laboratories, Alfred Nobel Drive Hercules, CA) was used at the final concentration of 25 ng cDNA. The expression levels of each gene were normalized to the levels of Gapdh using the ΔΔCt method and expressed as relative to mESC. Primers used for real time RT PCR are shown in Table 1 and Table 2. The results of real time RT PCR are shown in FIG. 14, and the results of RT-PCR are shown in FIG. 15.

Figure 14:
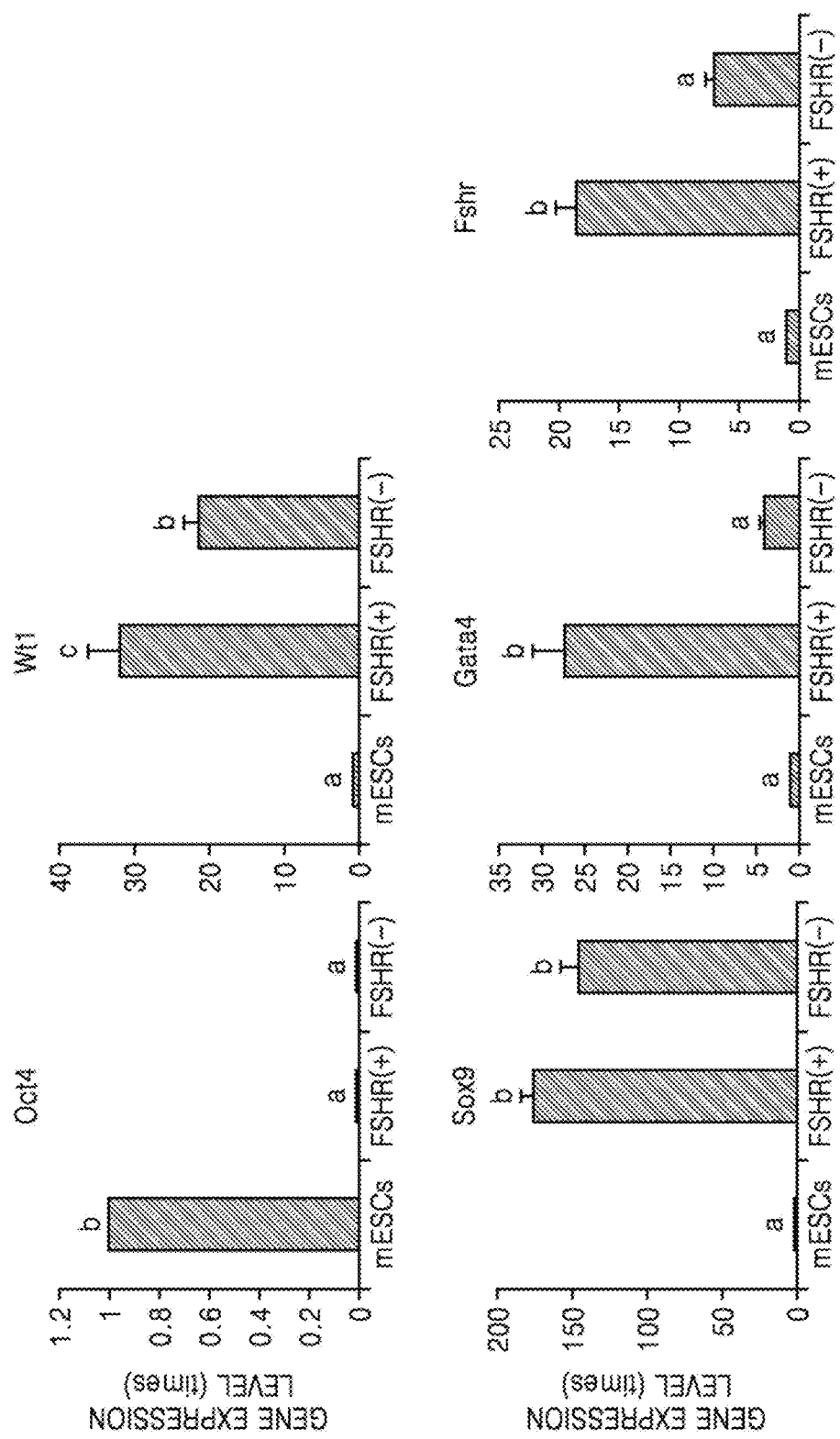
FIG. 14 shows a graph showing the results of real time PCR confirming mRNA expression levels of Oct4, Wt1, Sox9, Gata4, and Fshr genes in FSHR-positive SLC and FSHR-negative SLC; mESCs: mouse embryonic stem cells; FSHR(+): FSHR-positive SLC; FSHR(−): FSHR-negative SLC.
Figure 15:
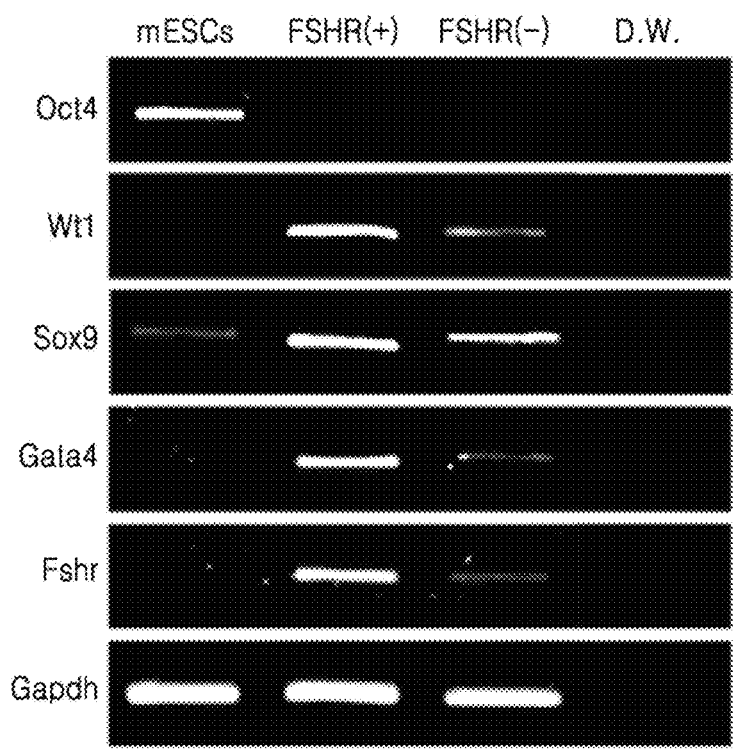
FIG. 15 shows images of the results of RT-PCR confirming mRNA expression levels of Oct4, Wt1, Sox9, Gata4, and Fshr genes in FSHR-positive SLC and FSHR-negative SLC; mESCs: mouse embryonic stem cells; FSHR(+): FSHR-positive SLC; FSHR(−): FSHR-negative SLC; D.W: Distilled water (control).

As shown in FIGS. 14 and 15, it was confirmed that mRNA expression levels of the sertoli cell markers Wt1, Sox9, Gata4, and Fshr were much higher in FSHR-negative SLC (FSHR (−)) than in FSHR-positive SLC (FSHR (+)).

Therefore, it was confirmed that FSHR-positive SLC expresses the characteristics of mature Sertoli cells.

Example 4. Functional Analysis of Induced SLC 4.1 Identification of Immunological Features of Induced SLC In order to confirm the immunological function of SLC induced from the present disclosure, Bululfan-treated ICR mouse was as the receptor animal. The receptor mice was anesthetized with avertin and the cell suspension (MACS-isolation cells) expressing EGFP described in the above example was injected in an amount of less than 10 µl at $1 \times 10^5$ cells/testicle, thereby transplanting cells into the seminiferous tubule via the export duct.

Figure 16:
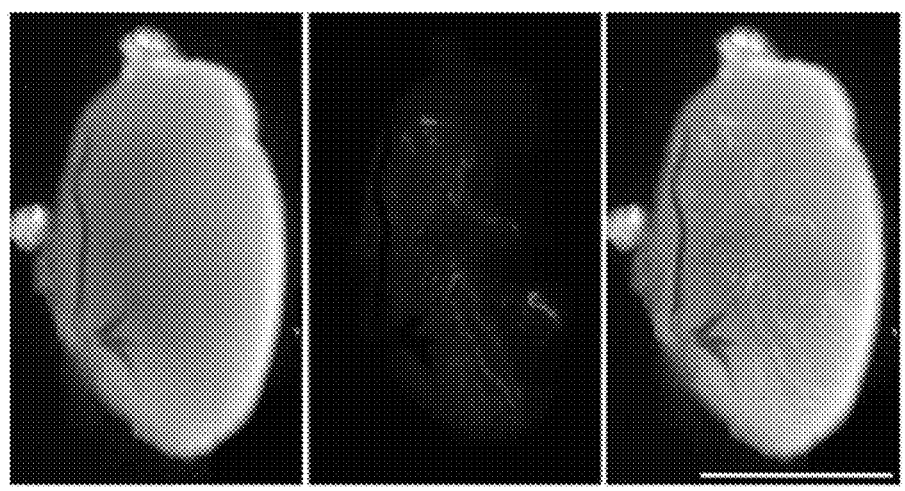
FIG. 16 shows images of a testicle and seminiferous tubule of a mouse of which EGFP expression was confirmed by ultraviolet (UV) light after SLC transplantation; Scale bar of 5 cm.

FIG. 16 shows images of a testicle and seminiferous tubule of a mouse of which EGFP expression was confirmed by ultraviolet (UV) light after SLC transplantation.

As shown in FIG. 16, it was confirmed that EGFP was expressed in the testicle and seminiferous tubule of the Busulfan-treated receptor mouse.

Therefore, it was confirmed that the SLC was well transplanted into the mouse testicle, and that SLC that was drived in vitro can be transplanted in vivo.

Figure 17:
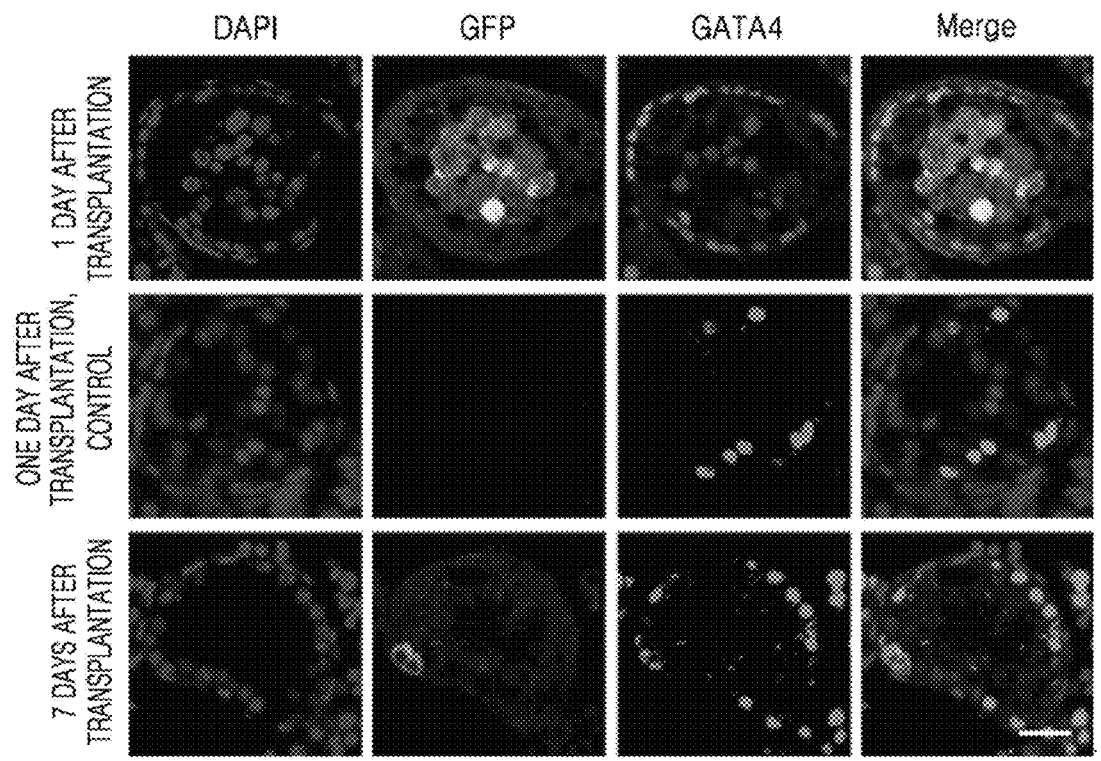
FIG. 17 shows the results of immunofluorescence of testicles stained with anti-GATA4 (red) and anti-GFP (green) antibodies 1 and 7 days after SLC transplantation; Scale bar of 20 μm.

FIG. 17 shows the results of immunofluorescence of testicles stained with anti-GATA4 (red) and anti-GFP (green) antibodies 1 and 7 days after SLC transplantation.

As shown in FIG. 17, it was confirmed by immunohistochemical analysis that a few EGF-positive SLCs were observed at the base of seminiferous tubule of receptor mound and co-expressed with SC marker GATA4. On day 1 after transplantation, clusters were detected in the seminiferous tubule of the testicle of the receptor mouse (top panel). On day 7 after transplantation, transplanted cells were located at the base of the seminiferous tubule of the receptor mouse (lower panel).

Therefore, it was confirmed that ESC-induced SLC can be transplanted into the seminiferous tubule of the receptor and, after transplantation, like Sertoli cells, located at the base of the seminiferous tubule and can functionally replace Sertoli cells.

4.2 Identification of Phagocytosis Activity of Induced SLC

In order to confirm the phagocytic activity of induced SLC according to the present disclosure, in vitro experiments were performed on Sertoli cells and induced SLC as follows.

With respect to adult SC, 5 day-old SC, induced SLC, FSHR-positive SLC, FSHR-negative SLC, and mouse embryonic fibroblasts (MEF), the uptake of fluorescein labeled E. coli was measured using a commercially available kit (Vybrant Phagocytosis Assay kit, Molecular Probes, Eugene, OR). Each cell was seeded in a 4-well plate at a concentration of $2 \times 10^5$ cells/well in s SLC differentiation medium at 5% $CO^2$ and at a temperature of 37° C. After 12 hours of inoculation, each cell was washed with PBS and incubated overnight in a SLC differentiation medium containing E. coli labeled with fluorescein. At the end of the incubation period, each cell was washed twice to remove E. coli that did not undergo extracellular phagocytosis, and a solution containing 100 ng/ml Hoechst (for staining cell nuclei; Thermo Scientific) in PBS was added in an amount of 0.5 ml to each well, followed by the incubation at a temperature of 37° C. for 15 minutes. Each cell was then washed twice with PBS. An image of each cell was obtained using a confocal microscope (Carl Zeiss LSM 880). Phagocytosis activity was measured with respect to cells having GFP particles/whole cells by using ImageJ (NIH, Bethesda, MD) software.

Figure 18:
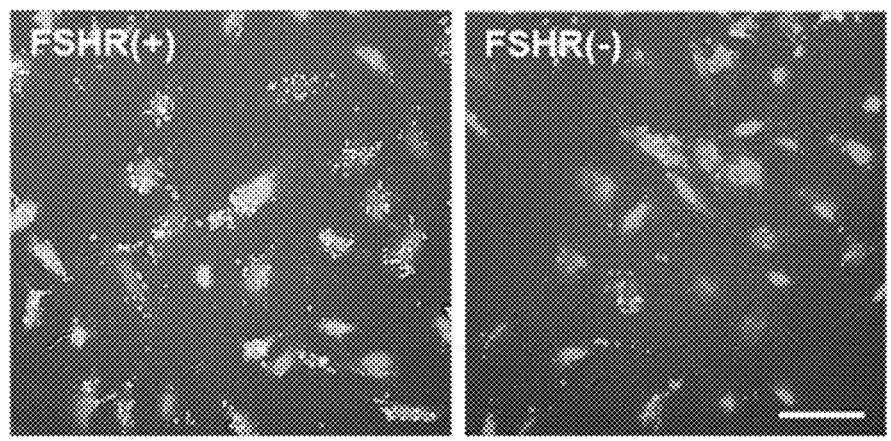
FIG. 18 shows images showing phagocytosis activity of FSHR-positive SLC (FSHR (+)) and FSHR-negative SLC (FSHR (−)). Blue: Hoechst-stained nucleus; Green: fluorescent microbeads; Red: induced SLC, derived from RFP-transplanted mESCs; FSHR (+): FSHR-positive SLC; FSHR (−): FSHR-negative SLC; Scale bar of 40 μm.

FIG. 18 shows images showing phagocytosis activity of FSHR-positive SLC (FSHR (+)) and FSHR-negative SLC (FSHR (−)). Blue: Hoechst-stained nucleus; Green: fluorescent microbeads; Red: induced SLC, derived from RFP-transplanted mESCs.

Figure 19:
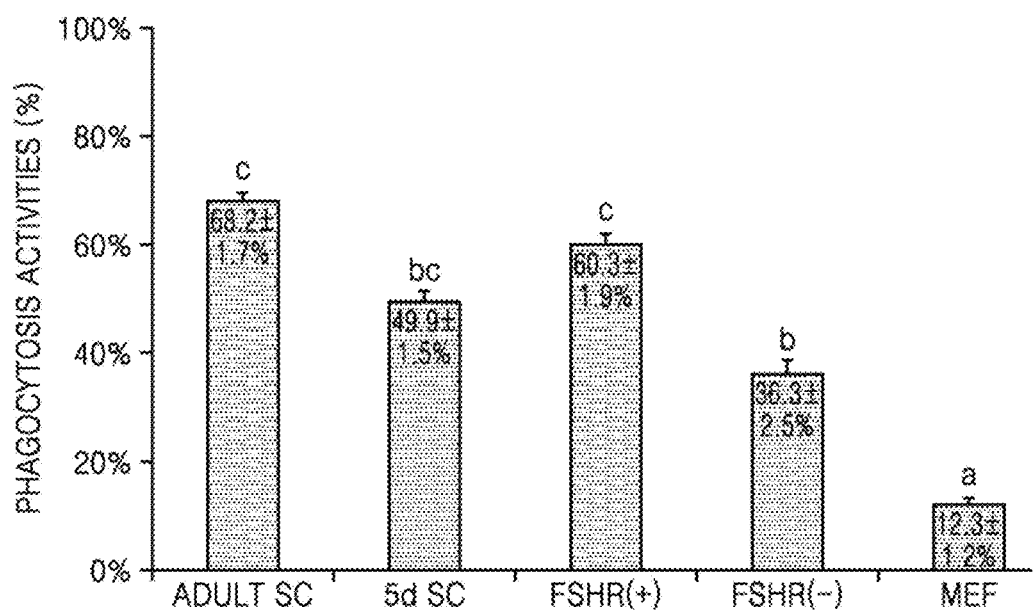
FIG. 19 shows a graph comparing phagocytosis activities of adult SC, 5-day old SC, FSHR-positive SLC, FSHR-negative SLC and MEF.

FIG. 19 shows a graph comparing phagocytosis activities of adult SC, 5-day old SC, FSHR-positive SLC, FSHR-negative SLC and MEF. Phagocytosis activity was calculated with respect to cells/whole cells (mean±SEM) containing fluorescent microbeads, with different alphabets representing $P<0.05$.

As shown in FIGS. 18 and 19, the phagocytosis activity of FSHR-positive SLC was significantly greater than MEF cells (somatic control) and FSHR-negative SLC, similar to that of the adult Sertoli cells.

4.3 Identification of CD4+ T Cell Proliferation Activity of Induced SLC (CD4+ T Cell Proliferation Assay)

In order to confirm CD4+ T cell proliferation activity through CFSE of induced SLC according to the present disclosure, the induced SLC and other cells were compared and analyzed as follows.

Splenocytes were isolated from 6 to 8 week-old male mouse, and erythrocytes were removed by adding erythrocyte lysate (Sigma). For isolation of CD4+ T cells, the cells were isolated using the CD4 T cell isolation kit (Miltenyi Biotecn) according to the manufacturer's method. Isolated CD4+ T cells were labeled with carboxyfluorescein diacetate succinimidyl ester (CFSC, BD bioscience). 1.2 µM of CFSE was labeled at a temperature of 37° C. for 10 minutes and washed three times at room temperature. CFSE-labeled CD4+ T cells were cocultured with splenocytes, human bone marrow induced mesenchymal stem cells (hBM-MSC, Lonza), adult SC, and induced SLC (FSHR (+)) at a 5:1 ratio for 5 days. To induce the proliferation of CD4+ T cells, 50 ng/ml of phorbol myristate acetate (PMA, Sigma) and 1 µM of ionomycin (Sigma) were co-cultured in culture. After co-culture, proliferative activity of CD4+ T cells was measured by flow cytometry (BD bioscience).

Figure 20:
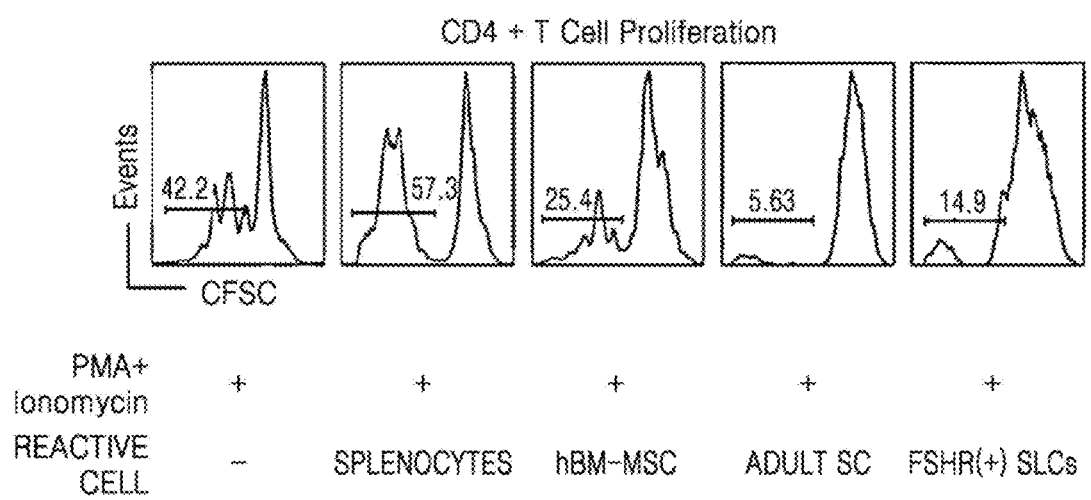
FIG. 20 shows a histogram measuring $CD4^+T$ cell proliferation via CFSE; hBM-MSCs: human bone marrow-induced mesenchymal stem cells; FSHR (+) SLCs: FSHR-positive SLC.

FIG. 20 is a histogram confirming CD4+ T cell proliferation activity through CSFE in splenocytes, hBM-MSC, adult SC, and induced SLC.

Figure 21:
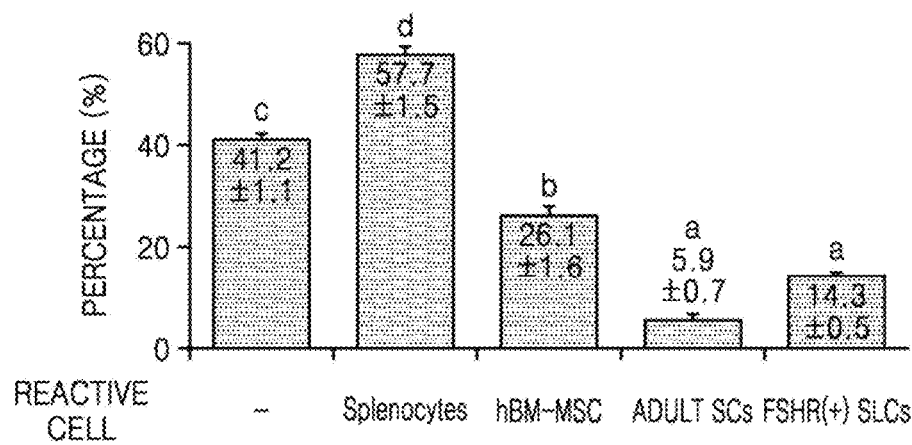
FIG. 21 shows a graph of the average value obtained by measuring $CD4^+$ T cell proliferation through CFSE. hBM-MSC: human bone marrow-induced mesenchymal stem cells; FSHR (+) SLCs: FSHR-positive SLC.

FIG. 21 is a graph showing the average value of the CD4+ T cell proliferation activities which were measured three or more times through CSFE in splenocyte, hBM-MSC, adult SC, and induced SLC. Different alphabets represent $P<0.05$.

As shown in FIGS. 20 and 21, the $CD^{4+}$ T cell proliferative activity of induced SLC was significantly lower than in a group treated with PMA and ionomycin to induce proliferation, splenocytes and hBM-MSC, and was similar to that of adult SC.

In addition, to determine whether the SLC according to the present disclosure exhibits sertoli cell-like functions, the mRNA expression level of Transferrin, which is a marker of Sertoli cells, and the mRNA expression level of TGF-β1, Il-6, Fas-L and Clusterin, which are immunomodulatory genes, were confirmed in un-isolated SLC, FSHR-positive SLC (FSHR (+) SLCs), and an adult testicle by real time PCR and RT-PCR. Primer sets used for real time PCR and RT-PCR are shown in Table 3 below.

TABLE 3

| Gene | Forward primer | Reverse primer |
|---|---|---|
| TGF-β1 | 5'-CCGCAACAACGCCA TCTATG-3' (SEQ ID NO: 21) | 5'-TGCCGTACAACTCCAG TGAC-3' (SEQ ID NO: 22) |
| Transferrin | 5'-TCTTCTCGGGCAGT TGTGTC-3' (SEQ ID NO: 23) | 5'-CATGAGAAGGGATCCG AGCC-3' (SEQ ID NO: 24) |
| Il-6 | 5'-AGCCAGABTCCTTC AGAGAGA-3' (SEQ ID NO: 25) | 5'-TGGTCTTGGTCCTTAG CCAC-3' (SEQ ID NO: 26) |
| Fas-L | 5'-GAACTGCGAGAACT CCGTGA-3' (SEQ ID NO: 27) | 5'-ACTCCAGAGATCAGAG CGGT-3' (SEQ ID NO: 28) |
| Clusterin | 5'-GGGTGTACTTGAGC AGAGC-3' (SEQ ID NO: 29) | 5'-TCCTTGGAATCTGGAG TCCGGT-3' (SEQ ID NO: 30) |

Figure 22:
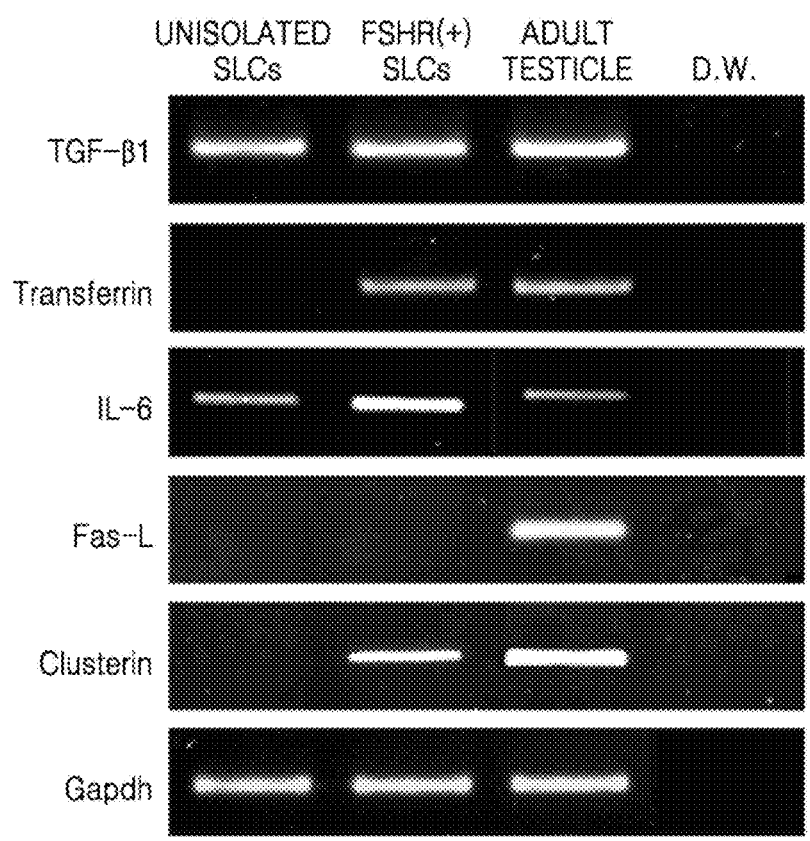
FIG. 22 shows the results of RT-PCR confirming mRNA expression levels of TGF-β1, Transferrin, IL-6, Fas-L and Clusterin in un-isolated SLC, FSHR-positive SLC, and adult testicles; FSHR(+) SLCs: FSHR-positive SLC; D.W; Distilled water (control).
Figure 23:
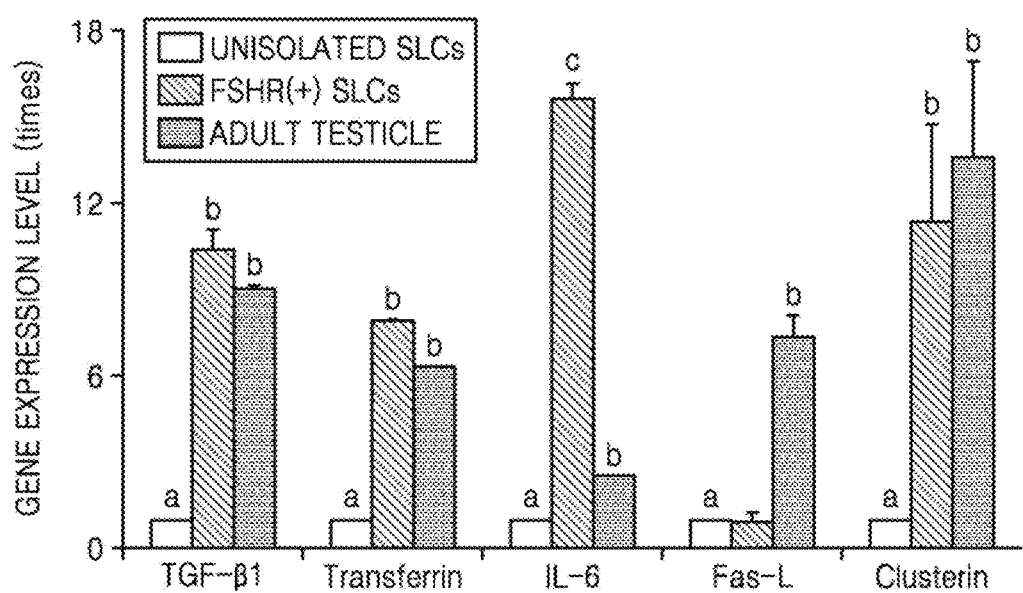
FIG. 23 illustrates the graph showing the results of real time-PCR confirming mRNA expression levels of TGF-β1, Transferrin, IL-6, Fas-L and Clusterin in un-isolated SLC, FSHR-positive SLC, and adult testicles; FSHR(+) SLCs: FSHR-positive SLC; D.W; Distilled water (control).

FIG. 22 shows the results of RT-PCR confirming mRNA expression levels of TGF-β1, Transferrin, IL-6, Fas-L and Clusterin in un-isolated SLC, FSHR-positive SLC, and adult testicles. As shown in FIG. 22, it was confirmed that Clusterin, Il-6 and TGF-β1 were highly expressed in FSHR-positive SLC and adult testicle tissues. In addition, the expression of Transferrin was detected in FSHR-positive SLC and adult testicle tissues.

Therefore, it was confirmed that due to the method according to the present disclosure, SLC induced in mESC has an immunosuppressive function and functional characteristics of mature Sertoli cells.

Statistical Analysis

Unless otherwise indicated, all data represent at least three independent experiments. The results were expressed as mean±SEM. Statistical significance was assessed using one-way ANOVA and Tukey test.

The invention claimed is:

1. A method of preparing Sertoli-like cells (SLC) from stem cells, the method comprising:
   inducing differentiation into intermediate mesoderm (IM) by culturing stem cells in a medium,
   wherein the inducing differentiation into the IM comprises culturing stem cells for one day to three days in the medium comprising a glycogen synthase kinase 3 (GSK-3) inhibitor, and additionally culturing for two days to five days after adding a base fibroblast growth factor (bFGF) and retinoic acid (RA) to the medium; and
   inducing differentiation into SLC by culturing the induced IM in a medium comprising bFGF, fibroblast growth factor 9 (FGF9), prostaglandin D2 (PDG2), follicle-stimulating hormone (FSH), and a glial cell-induced neurotrophic factor (GDNF),
   wherein the stem cells are embryonic stem cells (ESC).

2. The method of claim 1, wherein the medium comprising the GSK-3 inhibitor further comprises L-glutamine, antibiotics, or a combination thereof.

3. The method of claim 1, wherein in the inducing differentiation into SLC, the culturing period is five days to seven days.

4. The method of claim 1, wherein a concentration of the GSK-3 inhibitor is from 1 µM to 10 µM, a concentration of bFGF is from 50 ng/ml to 200 ng/ml, and a concentration of RA is from 0.5 µM to 1.5 µM.

5. The method of claim 1, wherein the embryonic stem cells are embryonic stem cells of a mouse.

6. The method of claim 1, further comprising isolating or purifying induced SLC.

* * * * *